(12) United States Patent
Azuma et al.

(10) Patent No.: US 7,404,797 B2
(45) Date of Patent: Jul. 29, 2008

(54) ULTRASONIC IMAGING SYSTEM AND ULTRASONIC SIGNAL PROCESSING METHOD

(75) Inventors: Takashi Azuma, Kawasaki (JP); Shinichiro Umemura, Hachiouji (JP); Tatsuya Hayashi, Kashiwa (JP); Kenichi Kawabata, Kodaira (JP); Akiko Osada, Tokyo (JP)

(73) Assignee: Hitachi Medical Corporation, Tokyo (JP)

(*) Notice: Subject to any disclaimer, the term of this patent is extended or adjusted under 35 U.S.C. 154(b) by 855 days.

(21) Appl. No.: 10/621,762

(22) Filed: Jul. 18, 2003

(65) Prior Publication Data

US 2004/0073112 A1    Apr. 15, 2004

(30) Foreign Application Priority Data

Oct. 9, 2002    (JP)    ............................. 2002-296183

(51) Int. Cl.
*A61B 8/00*    (2006.01)

(52) U.S. Cl. ...................................... 600/443; 600/437

(58) Field of Classification Search .................. 600/440, 600/443, 447, 441
See application file for complete search history.

(56) References Cited

U.S. PATENT DOCUMENTS

| | | | |
|---|---|---|---|
| 4,982,339 A * | 1/1991 | Insana et al. ................. | 600/437 |
| 5,050,226 A | 9/1991 | Collet-Billon | |
| 5,720,291 A * | 2/1998 | Schwartz ..................... | 600/456 |
| 5,793,883 A * | 8/1998 | Kim et al. .................... | 382/128 |
| 5,878,746 A * | 3/1999 | Lemelson et al. ............ | 600/407 |
| 5,961,461 A | 10/1999 | Mo et al. | |
| 6,193,660 B1 * | 2/2001 | Jackson et al. .............. | 600/443 |
| 6,283,918 B1 * | 9/2001 | Kanda et al. ................. | 600/441 |
| 6,413,219 B1 * | 7/2002 | Avila et al. .................. | 600/443 |
| 6,443,894 B1 * | 9/2002 | Sumanaweera et al. ...... | 600/443 |
| 6,511,426 B1 * | 1/2003 | Hossack et al. ............. | 600/437 |

FOREIGN PATENT DOCUMENTS

| | | |
|---|---|---|
| JP | 02-280739 | 11/1990 |
| JP | 11-197151 | 7/1999 |

* cited by examiner

*Primary Examiner*—Eleni Mantis Mercader
*Assistant Examiner*—Jacqueline Cheng
(74) *Attorney, Agent, or Firm*—Antonelli, Terry, Stout & Kraus, LLP.

(57) ABSTRACT

The present invention provides an ultrasonic imaging system capable of extracting structure-emphasized image data in which the structure of a tissue in a living body is emphasized and texture-emphasized image data in which a texture pattern coming from properties of a tissue in a living body is emphasized from B-mode image data, and obtaining a synthesized image obtained by weighting and combining the two extracted image data pieces. An ultrasonic imaging system has: a structure extractor for extracting structure-emphasized image data in which a structure of a tissue in the living body is emphasized from B-mode image data of the living body; a texture pattern extractor for extracting texture-emphasized image data in which a texture pattern coming from properties of a tissue in the living body is emphasized; an image synthesizer for obtaining a synthesized image by weighting and combining the structure-emphasized image data and the texture-emphasized image data; and a display for displaying at least one of the structure-emphasized image data, the texture-emphasized image data, and the synthesized image.

23 Claims, 15 Drawing Sheets

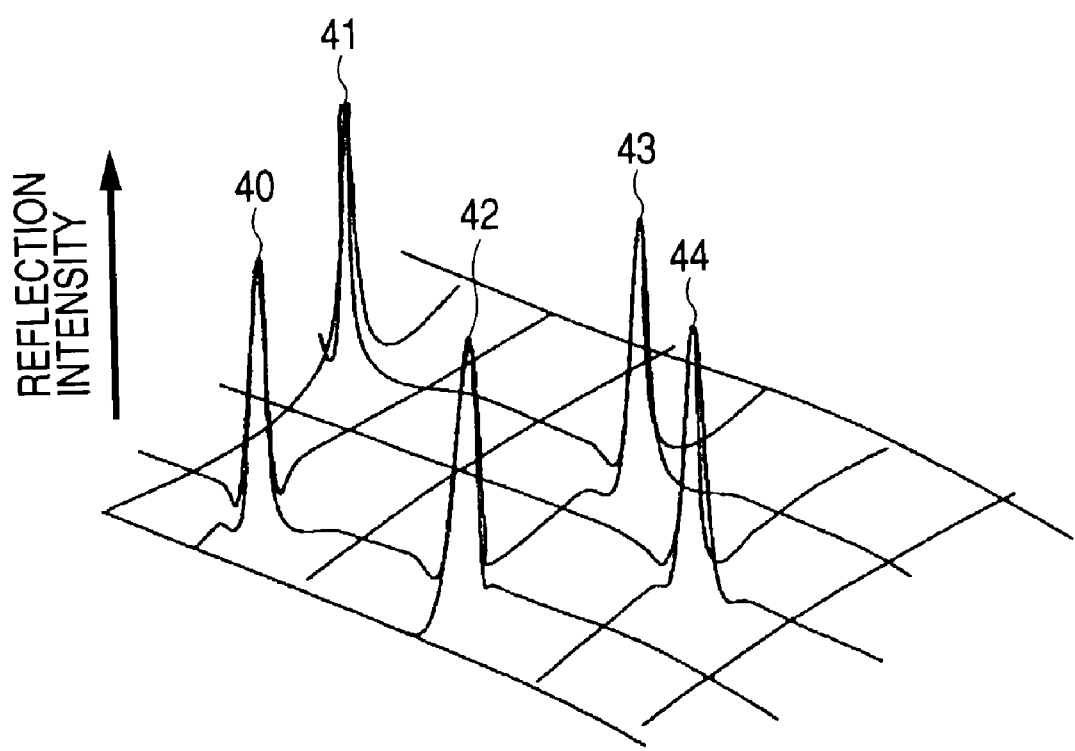

HISTOGRAM FOR DIFFERENCE OF INTENSITY

WEIGHTING FUNCTION W1

WEIGHTING FUNCTION W2

FIG. 8
(A) ORIGINAL IMAGE
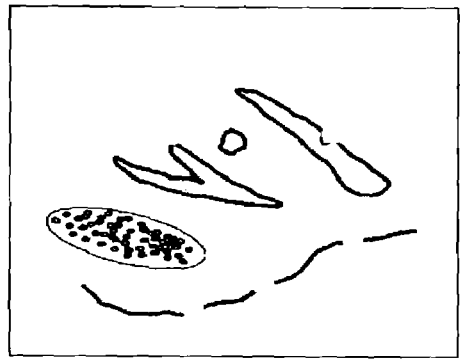
(B) STRUCTURE EMPHASIZED IMAGE
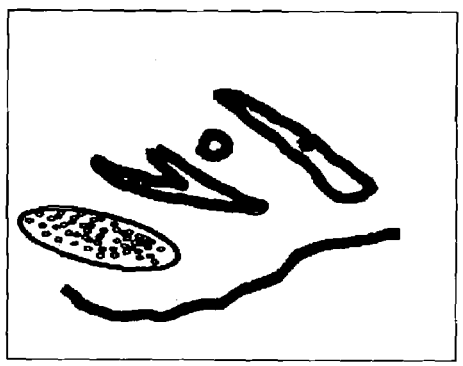
(C) TEXTURE EMPHASIZED IMAGE
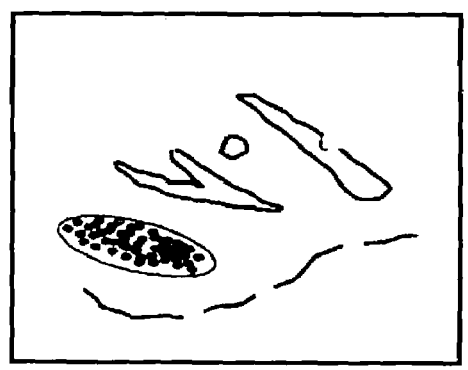
(D) COMBINED IMAGE OF (B) AND (C)
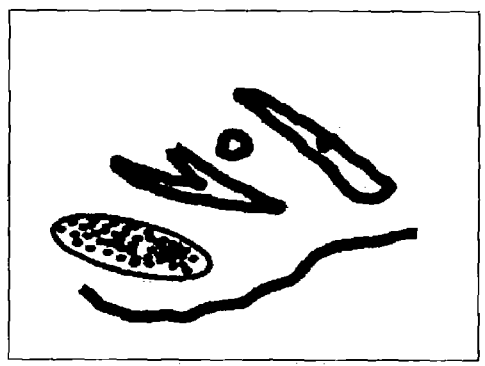

FIG. 15
(A) ORIGINAL IMAGE
(B) STRUCTURE EMPHASIZED IMAGE
(C) TEXTURE EMPHASIZED IMAGE
(D) COMBINED IMAGE OF (B) AND (C)

ULTRASONIC IMAGING SYSTEM AND ULTRASONIC SIGNAL PROCESSING METHOD

RELATED APPLICATIONS

The present application is related to and claims priority from Japanese Application No. 2002-296183 filed on Oct. 9, 2002.

BACKGROUND OF THE INVENTION

The present invention relates to an ultrasonic imaging system and an ultrasonic imaging method for generating images of a living body with ultrasonic waves.

An ultrasonic imaging system used for medical imaging diagnosis can display a tomographic image of a tissue of a soft part in a living body, an image of a blood flow in a living body, and the like in an almost real-time manner on a monitor by using the ultrasonic pulse echo method so that the images can be observed. Since a living body is not exposed to radiation which is used in an image diagnosing system, the ultrasonic imaging system is very safe. In addition, the system is small in size and cheap, so that it is used widely in the medical field.

An ultrasonic tomographic image (B-mode image) is an image indicative of the position of a reflector estimated from time required since ultrasonic waves are transmitted until an echo signal is received and intensity of the echo signal by transmitting ultrasonic waves to a living body and receiving an echo signal reflected from a region in the living body in which acoustic impedance changes spatially. It is known that peculiar artifact called speckle occurs in ultrasonic imaging. To improve the quality of an image, it is desirable to minimize the speckle.

Hitherto, a method and apparatus for adaptively enhancing a B-mode image has been proposed (for example, refer to Japanese Patent Application Laid-Open No. 11-197151). In the B-mode image enhancing apparatus, a low pass filter which smoothes out speckle and a high pass filter which enhances edges are placed in parallel signal paths connected to the output of an envelope detector. The signals in the high pass filter path are logarithmically compressed before high pass filtering. The signals in the low pass filter path are logarithmically compressed after low pass filtering. Respective weighting factors are applied to the low- and high-pass-filtered signals by an adaptive weighting means. The weighted low- and high-pass-filtered signals are summed and optionally input to an anti-aliasing filter before decimation and scan conversion.

A method of extracting a microstructure in an RF signal using statistical similarity has been proposed (for example, refer to Kamiyama et al., "Method for extracting micro-structure in RF signal using statistical similarity", Papers of Basic Technical Research of The Japan Society of Ultrasonics in Medicine, Dec. 22, 2001, Vol. 101, No. 4, pp. 14-18). The method is characterized in that by a spatial filtering for assigning a weight according to "similarity" in which Rayleigh probability density is assumed on a reception signal in a sample, a $\sigma$ value to be referred to is estimated, so that an influence of attenuation of a living body or the like can be avoided.

When the method was applied by using RF signals of a normal liver and a liver suffering cirrhosis, micro scatterers displaying non-Rayleigh scattering could be extracted while relatively maintaining drawing property of image diagnosis.

In the non-patent document 1 mentioned as an example of a conventional technique, a method of smoothing speckles by using "similarity" based on statistic in samples and statistically extracting a signal displaying non-Rayleigh scattering is proposed. In filtering using similarity in the method, a matrix of (M, N) pixels having a point $P_0$ (x, y) as a center in ultrasonic receive RF signals disposed in a two-dimensional matrix obtained by sequentially disposing one-dimensional data of scanning lines is assumed, and a weighting factor as expressed by Equation 1 is computed with respect to all of points $P_i$ in the matrix.

$$w_i = \{1 - ((I_i - I_0)/\alpha\sigma)^2\}^2 \qquad \text{Equation 1}$$

$I_i$ and $I_0$ denote amplitude values at points $P_i$ and $P_0$, respectively, $\sigma$ denotes a standard deviation in a sample, and $\alpha$ indicates an arbitrary filter factor. In the equation, when the inside of { } is negative, $w_i = 0$. By using $w_i$ obtained from Equation 1, an amplitude value at each point is multiplexed on the amplitude value at point $P_0$ as shown by Equation 2.

$$P_o \Rightarrow \Sigma P_i w_i / \Sigma w_i \qquad \text{Equation 2}$$

Although the filter is a smoothing filter in a broad sense, the filter is not related to distance between pixels. By Equation 2, the difference between amplitudes, that is, pixels having "similarity" are averaged.

FIGS. 1(A) and 1(B) are diagrams for explaining a problem to be solved by the invention and schematically illustrating reflection intensity of ultrasonic wave by continuous reflectors (structures).

FIG. 1(A) is a diagram schematically showing reflection intensity of ultrasonic waves by an interface between a structure—1(31) and a structure—2(32) which are continued in a living body. FIG. 1(B) is a diagram schematically showing reflection intensity of ultrasonic waves by an interface between a structure—3(33) and a structure—4(34) which are continued in a living body. 51 denotes a direction along the interface of the two structures, and 52 indicates a direction perpendicularly crossing the interface of the two structured.

FIG. 2 is a diagram for explaining a problem to be solved by the invention and schematically illustrating reflection intensity of ultrasonic waves by point reflectors 40, 41, 42, 43, and 44 which are scattered in a living body.

Reflection in a living body can be classified into the following two types (1) and (2).

(1) Reflection of ultrasonic waves by the interface (FIG. 1) of structures such as organs, blood vessel walls, tissues in an organ such as tumors, or thrombi in a blood vessel which are continued at least in one direction.

(2) Reflection by point reflectors (FIG. 2) which are not continued but are spread in a living body or the like.

In the following description, an image based on reflection intensity of the reflection (1) of ultrasonic wave, that is, an image (image in which a structure is reflected) obtained by emphasizing and extracting the structure of a living body tissue constructed by a set of point reflectors which are continuously distributed in at least one direction in the living body will be called a "structure-extracted image" or "structure-emphasized image". An image based on the reflection intensity of the reflection (2) of ultrasonic waves, that is, an image (image in which texture of a tissue is reflected) obtained by extracting components resulting from a reflector constructed by a set of point reflectors which are not continuously distributed in a living body but are spread will be called a "texture-extracted image" or "texture-emphasized image". A texture pattern resulting from properties of a tissue in a living body is one of living body information pieces and is utilized for diagnosis, as image information indicative of the properties of a tissue.

In the image acquisition using ultrasonic waves, in the case where the distribution of reflection intensity of ultrasonic waves from reflectors changes in a range almost equal to or smaller than width of point response function determined by the size of an aperture of transmit/receive wave, distance between the aperture and the reflector, and frequency of an ultrasonic pulse, echo signals from the reflectors interfere with each other, so that an interference pattern is multiplexed on an actual image in which the distribution of reflectors is reflected or the image is modulated by the interference pattern. It causes a problem such that the structure in the living body is not seen clearly.

As an attempt to make a structure in a living body clearly seen in an ultrasonic image, a method of removing the interference pattern has been examined. A normal linear filter has a drawback such that when efficiency of removing an interference pattern is increased, an edge of a structure is made blunt.

Generally, the spatial frequency in the distribution of reflectors in a structure is not always lower than that in the distribution of reflectors by which texture is obtained. The spatial frequency in the direction 52 perpendicularly crossing the interface of the two structures 33 and 34 shown in FIG. 1(B) is about the same as the spatial frequency of the distribution of reflectors from which texture is obtained. A change in intensity of an echo signal can occur at a high spatial frequency in the direction along the interface of the two structures 33 and 34. Therefore, although a B-mode image is adaptive emphasized by using two kinds of filters of a high-pass filter and a low-pass filter in the method described in Patent Document 1, it is difficult to satisfy both clear counter of a structure and removal of the interference pattern. It is improper to use a low-pass filter to eliminate an interference pattern from the viewpoint of picture quality. Regarding extraction of a structure in a living body and extraction of texture, the two kinds of filters do not correspond to the functions of an accelerator and a brake.

Although the filter described in the non-patent document 1 extracts a structure excellently, a problem occurs such that the filter erases a texture pattern. It is difficult to adjust the balance between extraction of a structure and extraction of a texture pattern which are mutually contradictory only by controlling the degree of extraction of a structure.

SUMMARY OF THE INVENTION

An object of the present invention is to provide an ultrasonic imaging system and method capable of extracting structure-emphasized image data in which the structure of a tissue in a living body is emphasized and texture-emphasized image data in which a texture pattern coming from properties of a tissue in a living body is emphasized from B-mode image data, and obtaining a synthesized image obtained by weighting and combining the two extracted image data pieces.

To achieve the object, the invention provides an ultrasonic imaging system for transmitting an ultrasonic pulse to a living body, receiving the ultrasonic pulse reflected by the living body, and obtaining B-mode image data of the living body, including: a structure extractor for extracting structure-emphasized image (structure-extracted image) data in which a structure of a tissue in the living body is emphasized from the B-mode image data; a texture pattern extractor for extracting texture-emphasized image (texture-extracted image) data in which a texture pattern coming from properties of a tissue in the living body is emphasized from the B-mode image data; an image synthesizer for obtaining a synthesized image by weighting and combining the structure-emphasized image data and the texture-emphasized image data; a display for displaying at least one of the structure-emphasized image data, the texture-emphasized image data, and the synthesized image; and means by which the operator can control the structure extractor and the texture extractor.

As the means by which the operator can control, the system has a parameter controller for setting parameters for signal processing into the structure extractor, the texture pattern extractor, and the image synthesizer on the basis of a distribution of signal intensities of pixels in the same frame of the B-mode image data.

The structure extractor extracts a structure of a living body tissue constructed by a set of point reflectors which are continuously distributed in at least one direction in the living body. The structure extractor is constructed by a nonlinear filter using similarity and has means for determining a region of peripheral pixels of each pixel in the B-mode image data, and means for obtaining a function for determining a weighting function on the basis of the difference between intensity of the each pixel and intensity of each of the peripheral pixels. The function has a maximum point when it is 0, and an integral value of an absolute value of the function in a region from negative infinity to positive infinity is finite. The weighting function for each of the peripheral pixels is determined from differentiation of the function. A value obtained by adding a sum of products of the weighting function and intensity of each of the peripheral pixels to intensity of each of pixels of the B-mode image data is used as signal intensity of each of pixels of the structure-emphasized image data.

The texture pattern extractor is constructed by a differential filter in two directions of signal intensities of pixels in the same frame of the B-mode image data and extracts a component coming from a reflector constructed by a set of point reflectors which are not continuously distributed in a living body but are spread.

BRIEF DESCRIPTION OF THE DRAWINGS

FIG. 2 is a diagram for illustrating a problem to be solved by the invention and schematically showing reflection intensity of ultrasonic waves by reflectors which are spread.

FIGS. 8(A) to 8(C) are diagrams for schematically illustrating an image change by a process of extracting a structure of a living body tissue, a process of extracting texture-emphasized image data, and a process of combining images obtained by the two extracting processes in the system of the first embodiment of the invention.

FIGS. 15(A) to 15(D) are diagrams showing an example of an image actually processed by a method of the invention.

DETAILED DESCRIPTION OF THE PREFERRED EMBODIMENTS

Embodiments of the invention will be described in detail hereinbelow with reference to the drawings.

First Embodiment

Figure 3:
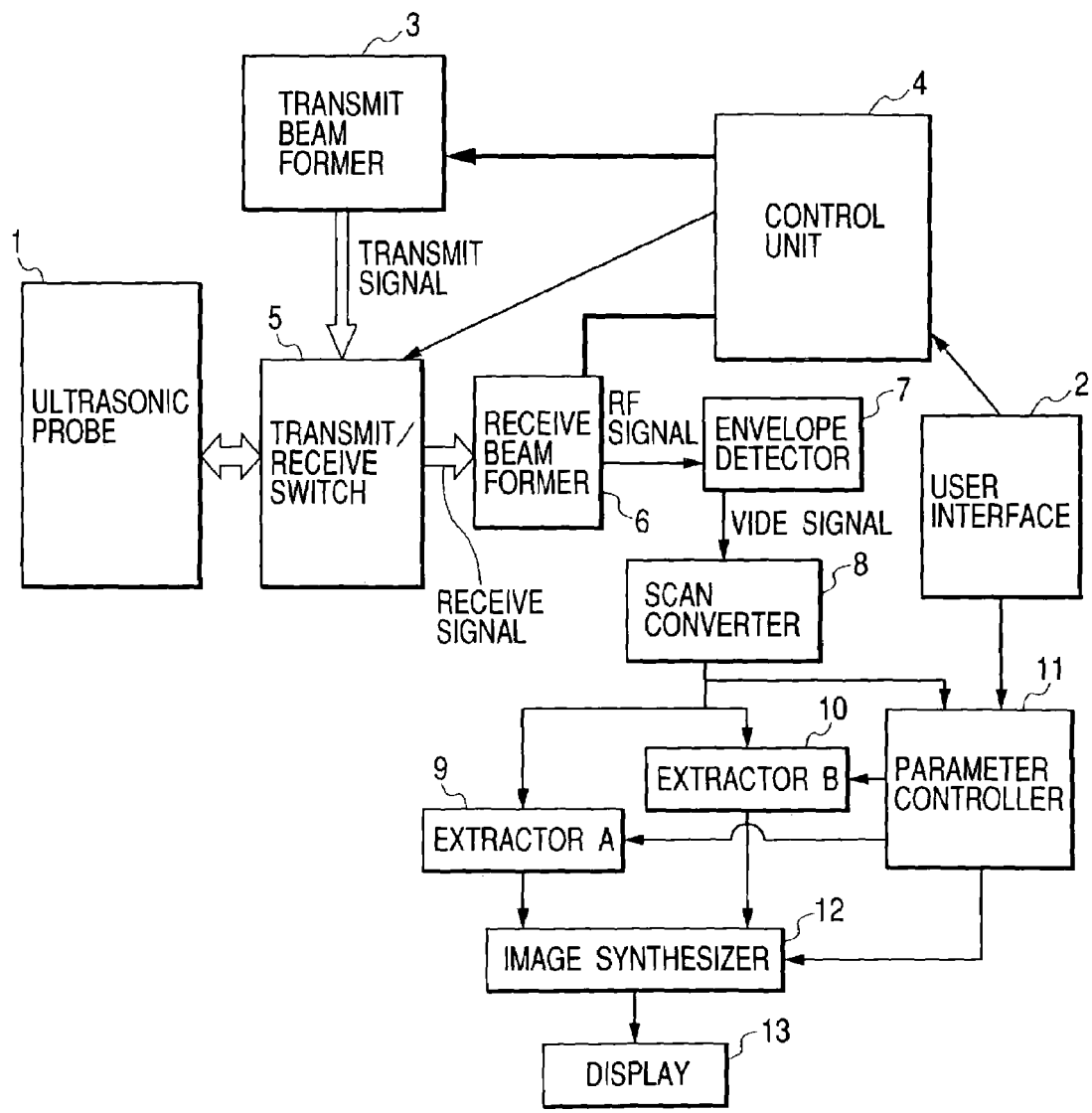
FIG. 3 is a diagram showing an example of the configuration of an ultrasonic imaging system of a first embodiment of the invention.

FIG. 3 is a diagram showing an example of the configuration of an ultrasonic imaging system of a first embodiment of the invention. An ultrasonic probe 1 in which ultrasonic elements are arranged one-dimensionally transmits an ultrasonic beam (ultrasonic pulse) to a living body (not shown) and receives an echo signal (reception signal) reflected by the living body. A transmit signal having delay time adjusted to the transmit focal point is output from a transmit beam former 3 under control of a control unit 4 and sent to the ultrasonic probe 1 via a transmit/receive switch 5 which is under control of the control unit 4. An ultrasonic beam (ultrasonic pulse) reflected or scattered in the living body and returned to the ultrasonic probe 1 is converted into an electric signal by the ultrasonic probe 1 and the electric signal is sent as a receive signal to a receive beam former 6 via the transmit/receive switch 5.

The receive beam former 6 performs dynamic focusing which adjusts the delay time in accordance with the timing of reception under control of the control unit 4. The receive beam former 6 is a complex beam former for mixing two receive signals whose phases are shifted by 90 degrees and outputs an. RF signal of a real part and an imaginary part. The RF signal is detected by an envelope detector 7 and is converted into a video signal. The video signal is input to a scan converter 8 where it is converted into image data (B-mode image data) The configuration described above is the same as that of a known ultrasonic imaging system.

In the system of the first embodiment, image data output from the scan converter 8 is sent to a structure extractor (extractor A) 9 and stored in a memory and is also sent to a texture extractor (extractor B) 10 and stored in a memory. If there is image data of the number of scanning lines equal to or larger than a region for calculation of weighting value in each extractor such as the case of using a processor which is good at performing pipeline calculation such as a digital signal processing (DSP) chip, without transferring all of image data of one tomographic image, calculation of weighting and calculation of an output value of the extractor is possible at that time point. Updating of data to be subjected to the extracting process each time image data on a new scanning line is obtained by acquisition of an image with ultrasonic waves is extremely effective means for real-time image display of the ultrasonic imaging system.

The structure extractor (extractor A) 9 extracts the structure of a living body tissue constructed by a set of point reflectors continuously distributed in at least one direction in a living body from the B-mode image data. That is, structure-emphasized image data in which the structure of a tissue in a living body is emphasized is extracted. The texture extractor (extractor B) 10 extracts a component coming from the reflector constructed by a set of point reflectors which are spread without being continuously distributed in a living body from the B-mode image data. That is, texture-emphasized image data in which a texture pattern related to the properties of a tissue in a living body is emphasized is extracted. An image synthesizer 12 combines the structure-emphasized image data and the texture-emphasized image data, thereby obtaining a synthesized image. The synthesized image is sent to a display 13 and displayed.

A parameter controller 11 sets parameters for signal processing in the structure extractor (extractor A) 9, texture extractor (extractor B) 10, and image synthesizer 12 to the components. The parameters are input by the operator from a user interface 2 and output from the parameter controller 11. The user interface 2 has an input knob used to set a parameter of selecting either the structure or texture of a tissue in a living body to be emphasized more.

In such a manner, not only parameters of the system but also the parameters for imaging of the operator are set by the user interface 2. An object to be extracted differs according to an object of diagnosis such as the structure of an object such as the outline of a thrombus in a blood vessel, a texture pattern in which the properties of a liver tissue like a progress of liver cirrhosis of a liver is reflected, both of the structure and texture like a cancer tissue in a living body, or the like. Consequently, setting of parameters by the operator regarding the object of imaging is very effective.

When the target of imaging or the object of diagnosis is selected by the operator with the user interface 2, the parameters of imaging such as frequency, gain, transmit focal position, and the like are adjusted. Alternately, a method such that, when the target of imaging or the object of diagnosis is selected with the user interface 2, default values of the parameter of the degree of extraction of structure-emphasized image data and the parameter of the degree of extraction of texture-emphasized image data are optimized and fine adjustment is made by the operator is also a method effective to improve ease of use of the operator.

In an example of the configuration of the system shown in FIG. 3, parameter setting based on the B-mode image data output from the scan converter 8 to the parameter controller 11 and stored in the memory is also made.

The parameter controller 11 calculates statistical information of the B-mode image data. The statistical information is, as will be described later, a width of frequency distribution of the luminance differences. Each of the luminance differences with respect to all of target pixels in the extracting process is the difference between intensity ($I_o$) of a target pixel of the process of extracting the structure of a living body tissue in the structure extractor (extractor A) 9 and intensity ($I_{ij}$) of a pixel in a region for calculation of weighting values around the target pixel of the extracting process (target region for calculation of weighting values includes peripheral pixels i=1, 2, . . . , $i_{max}$ and j=1, 2, . . . , $j_{max}$ of the target pixel of the extracting process). The width of the frequency distribution of the intensity differences is used for setting a weighting function which will be described later.

Figure 4:
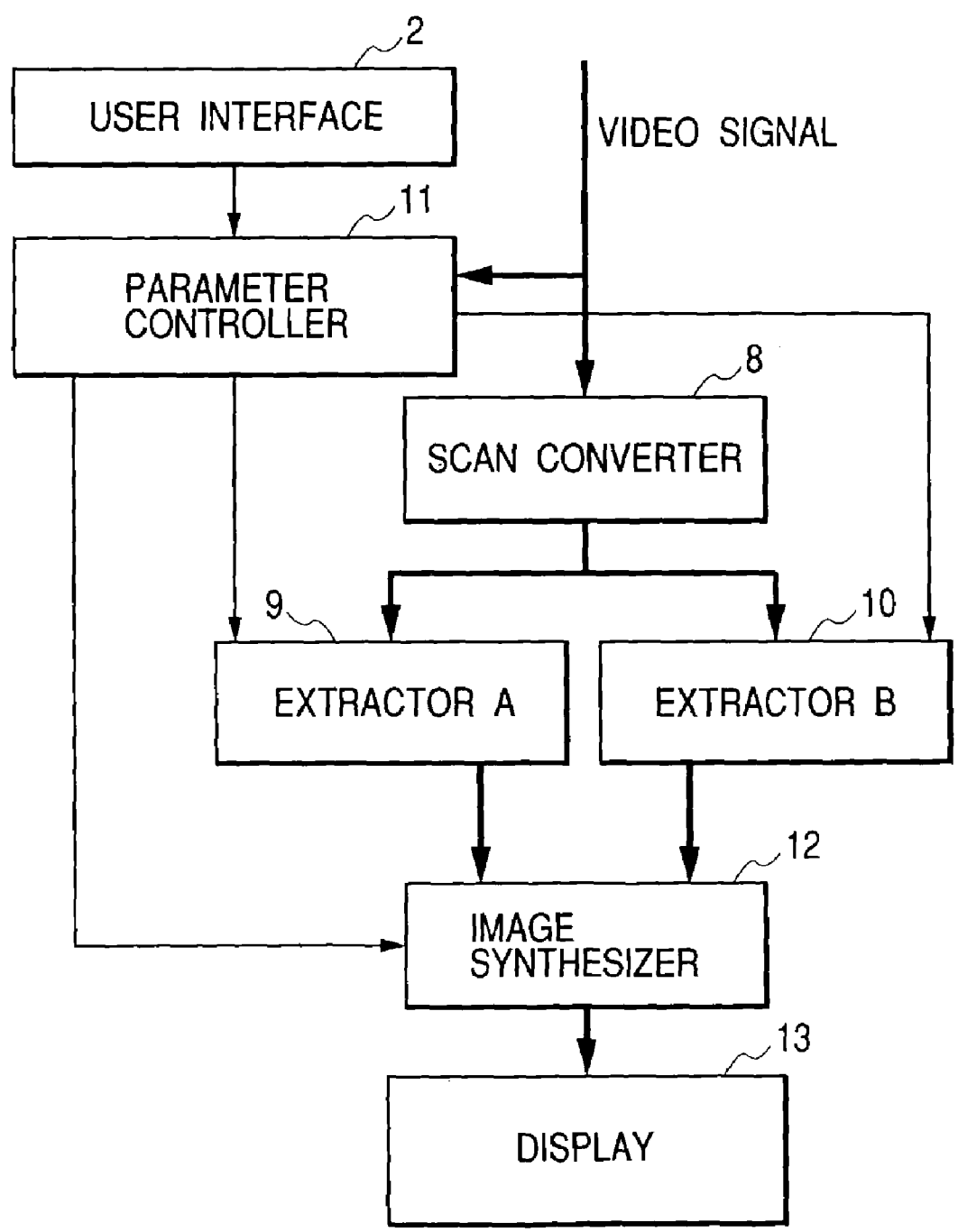
FIG. 4 is a diagram showing a modification of the first embodiment of the invention.

FIG. 4 is a diagram showing a modification of the first embodiment of the invention illustrated in FIG. 3. In place of outputting the B-mode image data from the scan converter 8 to memory in the parameter controller 11, a video signal output from the envelope detector 7 is output to the memory in the parameter controller 11. The parameter controller 11 calculates statistic information of the video signal, that is, the width of the frequency distribution of the difference of intensity. In FIG. 4, a video signal is the video signal output from the envelope detector 7 shown in FIG. 3.

Figure 5A:
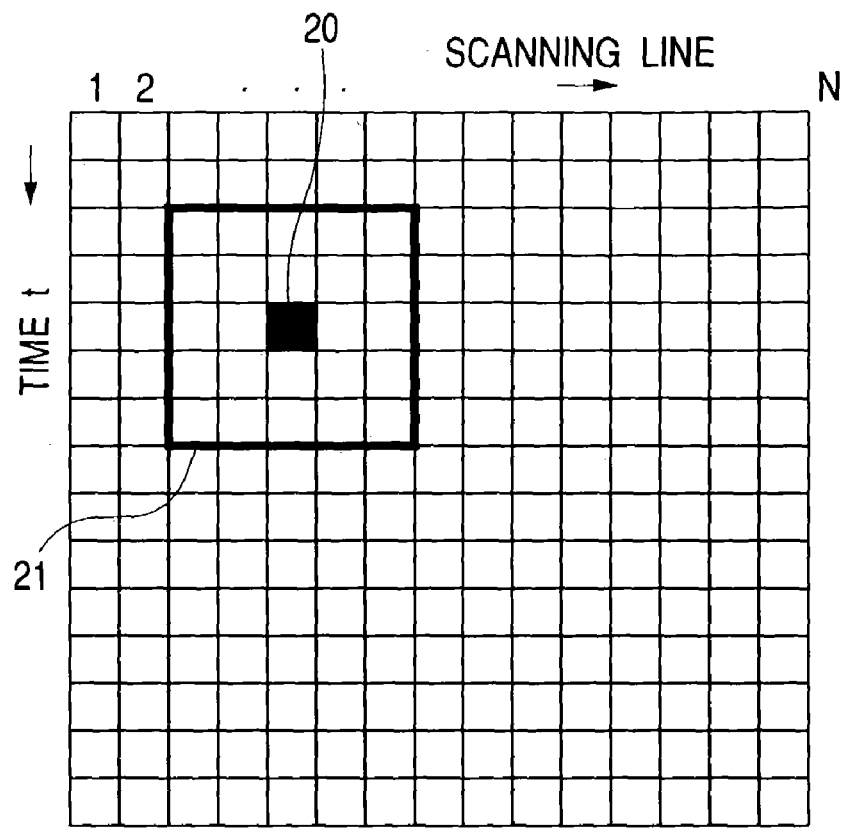
FIGS. 5(A) and 5(B) are diagrams showing a target pixel of a process of extracting a structure of a living body tissue in a structure extractor (extractor A) of the first embodiment of the invention and a region for calculation of weighting value.
Figure 5B:
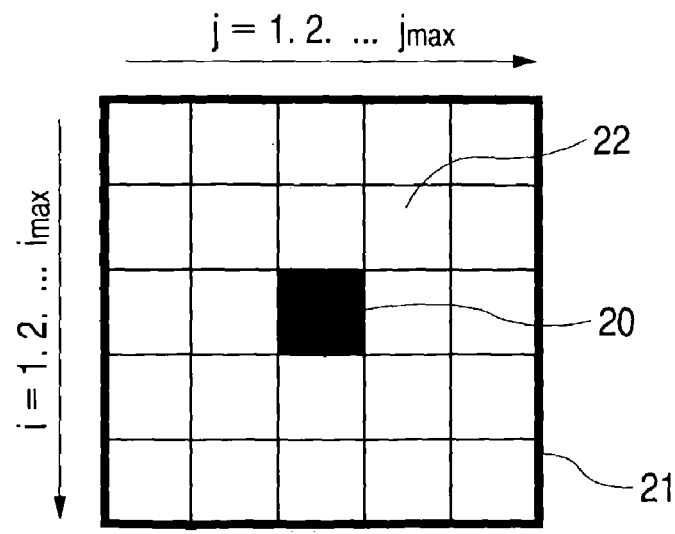

FIGS. 5(A) and 5(B) are diagrams illustrating a target pixel of the process of extracting a structure of a living body tissue in the structure extractor (extractor A) 9 of the first embodiment of the invention and a region for calculation of weighting values.

Figure 6:
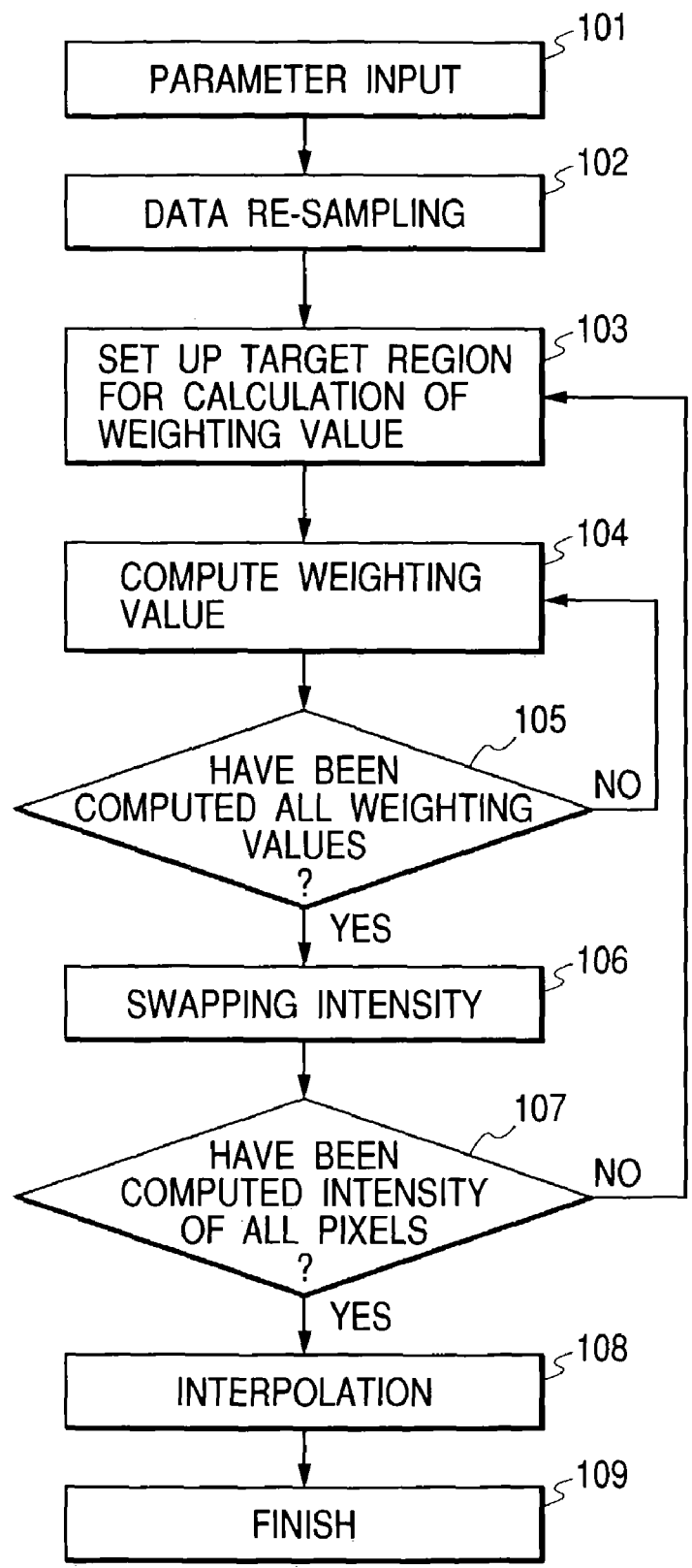
FIG. 6 is a flowchart of the process of extracting a structure of a living body tissue in the structure extractor (extractor A) of the first embodiment of the invention.

FIG. 6 is a flowchart of the process of extracting the structure of a living body tissue in the structure extractor (extractor A) 9 of the first embodiment of the invention.

In the memory of the structure extractor. (extractor A) 9, as shown in FIG. 5(A), two-dimensional data obtained by arranging one-dimensional image data of scanning lines 1, 2, ... and N each of which changes in the direction of the time base "t" into the direction of the scanning lines is stored as objects to be subjected to the process of extracting the structure of a living body tissue. A region 21 for calculating weighting value, which surrounds a target pixel (having intensity $I_0$) 20 of the process of extracting the structure of a living body tissue in the structure extractor (extractor A) 9 is set.

FIG. 5(B) is an enlarged view of the region 21 for calculation of weighting value shown in FIG. 5(A). The region 21 for calculation of weighting values includes peripheral pixels 22 ($i_{max} \times j_{max}$ pixels having intensity $I_{ji}$) of the target pixel 20 of the extracting process, consisting of i pixels (i=1, 2, ..., $i_{max}$)×j pixels (j=1, 2, ..., $j_{max}$). The larger the region of calculation of weighting values is, the larger the effect of the structure extracting filter is. However, the computation speed accordingly decreases.

In place of enlarging the region for calculation of weighting values, it is also effective to improve efficiency of calculation by performing a decimation process (process of binding data of a plurality of pixels continued in each of the direction of the time base "t" and the arrangement direction of the scan lines with two-dimensional data as a target on which the process of extracting the structure of a living body tissue is to be performed). After the process of extracting the structure of a living body tissue is finished with respect to all of pixels in the two-dimensional data obtained by the binding addition, the number of pixels of the original two-dimensional data before the binding addition is reset by an interpolating operation using the two-dimensional data obtained by the binding addition subjected to the process of extracting the structure of a living body tissue.

The number of re-sample points in the decimation process, $i_{max}$ and $j_{max}$, and the shape of weighting function is set in the parameter input step 101 in FIG. 6. In the parameter input step 101, the width of a histogram of the difference of intensity obtained by calculating the difference between intensity ($I_0$) of the target pixel of the process of extracting the structure of a living body tissue and the intensity ($I_{ij}$) of a pixel in the region for calculation of weighting values surrounding the target pixel of the extracting process with respect to all of target pixels of the extracting process. The width of a histogram of the difference of intensities is used to set a weighting factor which will be described later.

In data re-sampling step 102, data is re-sampled. In weighting value calculation region setting step 103, pixels in a region for calculation of weighting value determined by the position of the target pixel of the process of extracting the structure of a living body tissue and $i_{max}$ and $j_{max}$ are set. In weighting values computing step 104, calculation of weighting values is executed on the basis of a weighting function which will be described later. When it is determined in weighting value calculation end determining step 105 that the calculation has been performed on all of pixels in the weighting value calculation region, in intensity swapping step 106, intensity to be set for the target pixel of the extracting process is derived. When it is determined in target pixel computation end determining step 107 that computation has been performed on all of the pixels in the two-dimensional data to be subjected to the process of extracting the structure of a living body tissue by shifting the position of the target pixel of the extracting process, in data interpolating step 108, data interpolation is performed to convert the data re-sampled in the data re-sampling step 102 and, after that, the structure extracting process is finished in step 109.

Figure 7A:
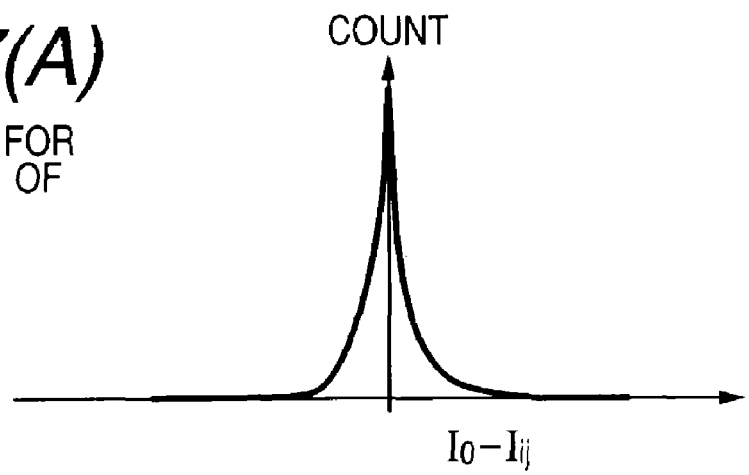
FIGS. 7(A) to 7(C) are diagrams illustrating a weighting function of the structure extraction filter used for the process of extracting a structure of a living body tissue in the system of the first embodiment of the invention.
Figure 7B:
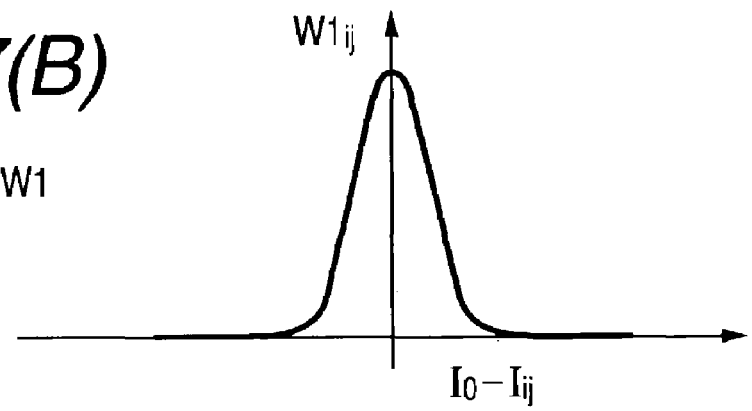
Figure 7C:
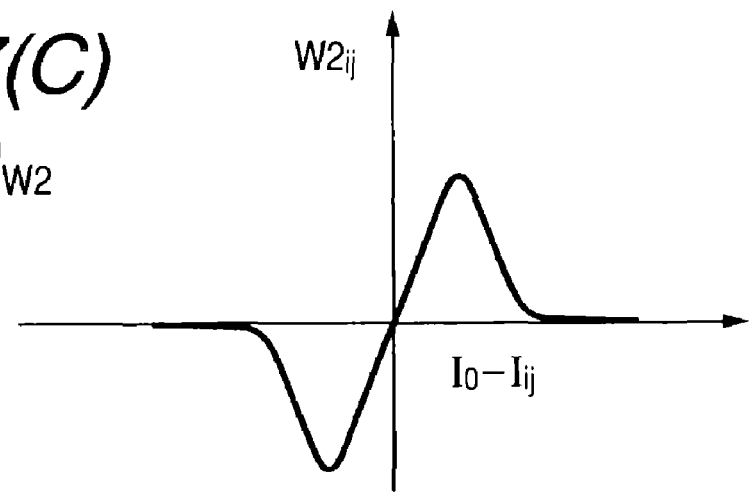

FIGS. 7(A) to 7(C) are diagrams showing weighting functions of a structure extraction filter used for the process of extracting the structure of a living body tissue in the system of the first embodiment of the invention. FIG. 7(A) is a diagram showing a histogram for difference of intensity described above in a typical ultrasonic image. The horizontal axis indicates the intensity difference ($I_0-I_{ij}$), and the vertical axis denotes the number of appearing times of the intensity difference ($I_0-I_{ij}$).

FIG. 7(B) shows an example of a weighting function W1 that a weight decreases monotonously as the absolute value of the intensity difference ($I_0-I_{ij}$) increases. In correspondence with the value of the lateral axis ($I_0-I_{ij}$), a weight $W1_{ij}$ is calculated. As an example of the weighting function W1, various even functions are possible such as an even-order polynomial of Equation 1 in the non-patent document 1, a Gaussian function, and a function like $1/(x^2+a^2)$. However, when a filter calculation is executed by a dedicated computing circuit in a real-time manner, the weighting function requires higher development like an exponential function. Further, when division is included, the number of calculation times of the sum of products increases. Consequently, there is the possibility that need for the ultrasonic diagnosis of performing real-time imaging is not satisfied.

FIG. 7(C) shows a weighting function W2 of the structure extraction filter used in the first embodiment of the invention. In correspondence with the value ($I_0-I_{ij}$) of the lateral axis, a weighting function $W2_{ij}$ is calculated. The weighting function W2 is an odd function obtained by differentiating the function W1.

In the first embodiment, from the histogram for difference of intensity shown in FIG. 7(A), the function W1 for determining the weighting function W2 is determined. The function W1 has the maximum point when ($I_0-I_{ij}$)=0, and an integral value of the absolute value W1 of the functions in the range from the negative infinity to the positive infinity is finite. $\Sigma$ in the denominator of Equation 2 is for all of pixels in the region for calculating a weight also including the target pixel of the extracting process. However, the value of $W_{ij}$ varies according to pixels, so that the value varies each time and calculation of division is required. In the case of performing a high-speed pipeline process in a DSP or the like, computation of division of once requires computation of the sum of products of the number corresponding to precision necessary for the division. Consequently, to perform the process in a real-time manner as in the ultrasonic imaging system, it is necessary to use an algorithm which does not include division. When approximation in which the denominator can be regarded as a constant exists, by executing multiplication of an inverse number as division of a constant, computation time can be shortened.

As a method for realizing it, first, as shown in Equation 3, a part related to $I_0$ is taken out from a fraction. When $\Sigma$ in the numerator in Equation 3 is regarded as a new weighting function, the function shown in FIG. 7(C) becomes the new weighting function W2 which is obtained by differentiating the function W1. Since the denominator is a normalized factor by the sum of weighting, in the case of the function W2 of which integral value becomes 0, necessity of normalization decreases. It is predicted that even if approximation for making the denominator regarded as a constant is performed, influence of the approximation can be ignored. The fact was proved by study using an actual image. Therefore, since approximation like Equation 4 is generally possible, division can be omitted. As $W_0$, for example, a value proportional to $i_{max} \times j_{max}$ is used. If the constant $W_0$ is multiplied with a coefficient, it is equivalent to a calculation that the numerator is divided by the coefficient. Consequently, the value of $W_0$ is not unconditionally determined. As long as calculation is based on the idea, if Equation 4 is not changed as a whole even when the value of $W_0$ is changed, the result is obviously the same. Further, as $W_0$, a value depending on $i_{max}$, $j_{max}$ can be used (for example, $i_{max}+j_{max}$).

$$\Sigma I_{ij}W_{ij}/\Sigma W_{ij}=I_0+\Sigma\{(I_{ij}-I_0)W_{ij}\}/\Sigma W_{ij} \quad \text{Equation 3}$$

$$\Sigma I_{ij}W_{ij}/\Sigma W_{ij}\approx I_0+W_0^{-1}\Sigma\{(I_{ij}-I_0)W_{ij}\} \quad \text{Equation 4}$$

Figure 1A:
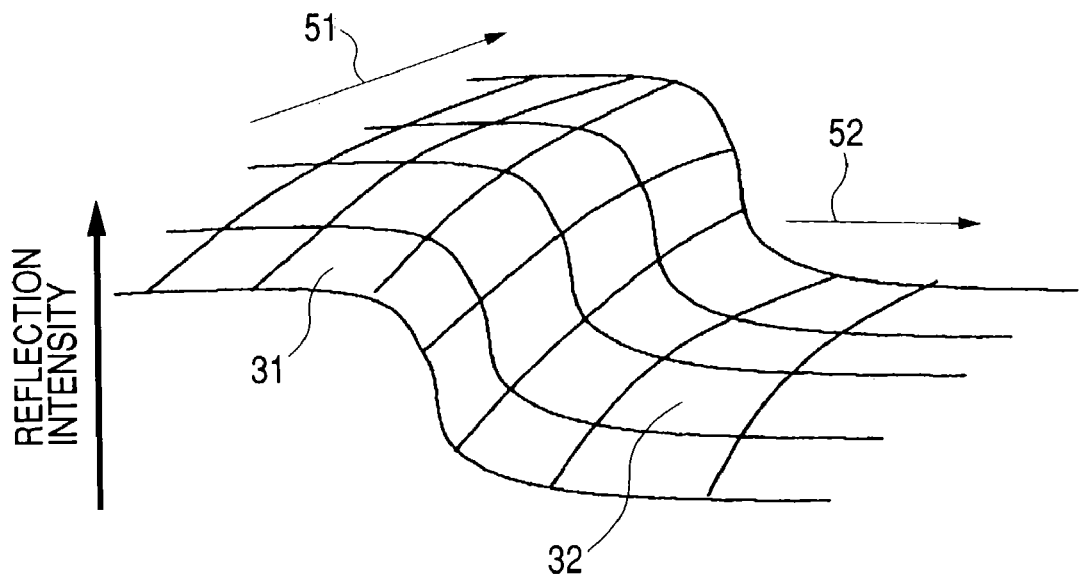
FIGS. 1(A) and 1(B) are diagrams for illustrating a problem to be solved by the invention and schematically showing reflection intensity of ultrasonic waves by continuous reflectors (structures).
Figure 1B:
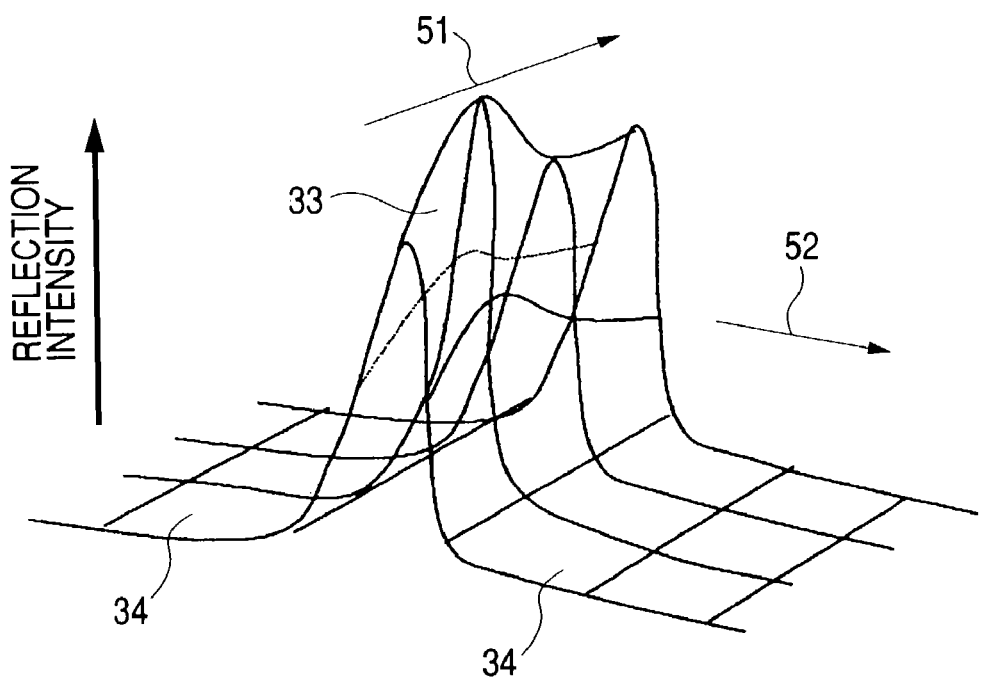

The function of the filter shown in Equation 4 varies according to continuity of intensity of a pixel to those of peripheral pixels. When the difference between intensity $I_0$ and the intensity $I_{ij}$ of the peripheral pixel is small, the weighting value is almost constant, so that the filter functions as a two-dimensional low-pass filter. In the case where a pixel having intensity $I_0$ is positioned in the interface of two structures (tissues), the weighting values to pixels along the interface of the two structures are large as shown in FIG. 1. In a direction 51 along the interface of two structures, the filter functions as a one-dimensional low-pass filter. In a direction 52 which perpendicularly crosses the interfaces of two structures, the filter functions as an all-pass filter, so that the sharpness of the interface does not deteriorate. As described above, by using non-linear filters of different functions in accordance with the shape of the distribution of intensity of pixels, a structure in a living body can be extracted. By executing approximation according to Equation 4, normalization performed with the sum of weighting values becomes unnecessary and computation of multiplication with a constant is sufficient. The weighting function of FIG. 7(C) can be expressed in various forms. There is also a method of using a table of weighting functions.

In the texture extractor (extractor B) 10 for extracting texture-enhanced image data in which a texture pattern that comes from the properties of a tissue in a living body is emphasized, it is desirable to use a spatial differential filter (high-pass filter in expression in frequency space) from the viewpoint of performance and computation speed. Generally, texture emphasis is achieved by multiplying each of two directions of the vertical and horizontal directions of two-dimensional data on which the texture-emphasized image data extracting process is to be performed with a matrix [1 −1] of one row and two columns as a differential filter. It is also effective to change the size of the differential filter in accordance with the shape of a point response function or change the intensity of the differential filter between the vertical direction (direction of the scanning line t) and the horizontal direction (direction in which the scanning lines are arranged).

FIGS. 8(A) to 8(D) are diagrams schematically illustrating changes in an image by a process of combined images obtained by two extracting processes of the process of extracting the structure of a living body tissue and the process of extracting texture-emphasized image data in the system of the first embodiment of the invention. FIG. 8(A) shows an original image (B-mode image), FIG. 8(B) shows a structure-emphasized image obtained by the structure extractor (extractor A) 9, and FIG. 8(C) shows a texture-emphasized image obtained by the texture extractor (extractor B) 10. An example of result of application to an actual living body will be described later (FIG. 15).

In the original image of FIG. 8(A), both the shape of the structure and texture of a living body tissue are unclear. By combining a structure-emphasized image (image in which the structure of the tissue in a living body is emphasized) of FIG. 8(B) and the texture-emphasized image (texture-emphasized image in which a texture pattern that comes from the properties of the tissue in a living body is emphasized) of FIG. 8(C), an image having both characteristics of the emphasized structure and texture of the tissue in a living body is obtained.

The image synthesizer 12 also has the function of adjusting an intensity compression curve. The structure-emphasized image of FIG. 8(B) and the texture-emphasized image of FIG. 8(C) are combined with the shape of a compression curve of components emphasizing the structure of a tissue in a living body and the shape of a compression curve of texture components. Generally, it is difficult to adjust two contradictory components of the components emphasizing the structure of the tissue in a living body and the components emphasizing the texture by using only one original image. Particularly, it is extremely difficult in the case where a plurality of parameters such as the compression curves are involved in the imaging process.

The method of the present invention relates to an imaging process performed after ultrasonic waves are transmitted/received to/from a living body. Therefore, the picture quality can be also adjusted in the form adapted to the aim of observation of the operator by changing the parameters of the structure emphasis and the texture emphasis on a single tomographic image after completion of image acquisition (that is, transmission and reception of ultrasonic waves).

Figure 13:
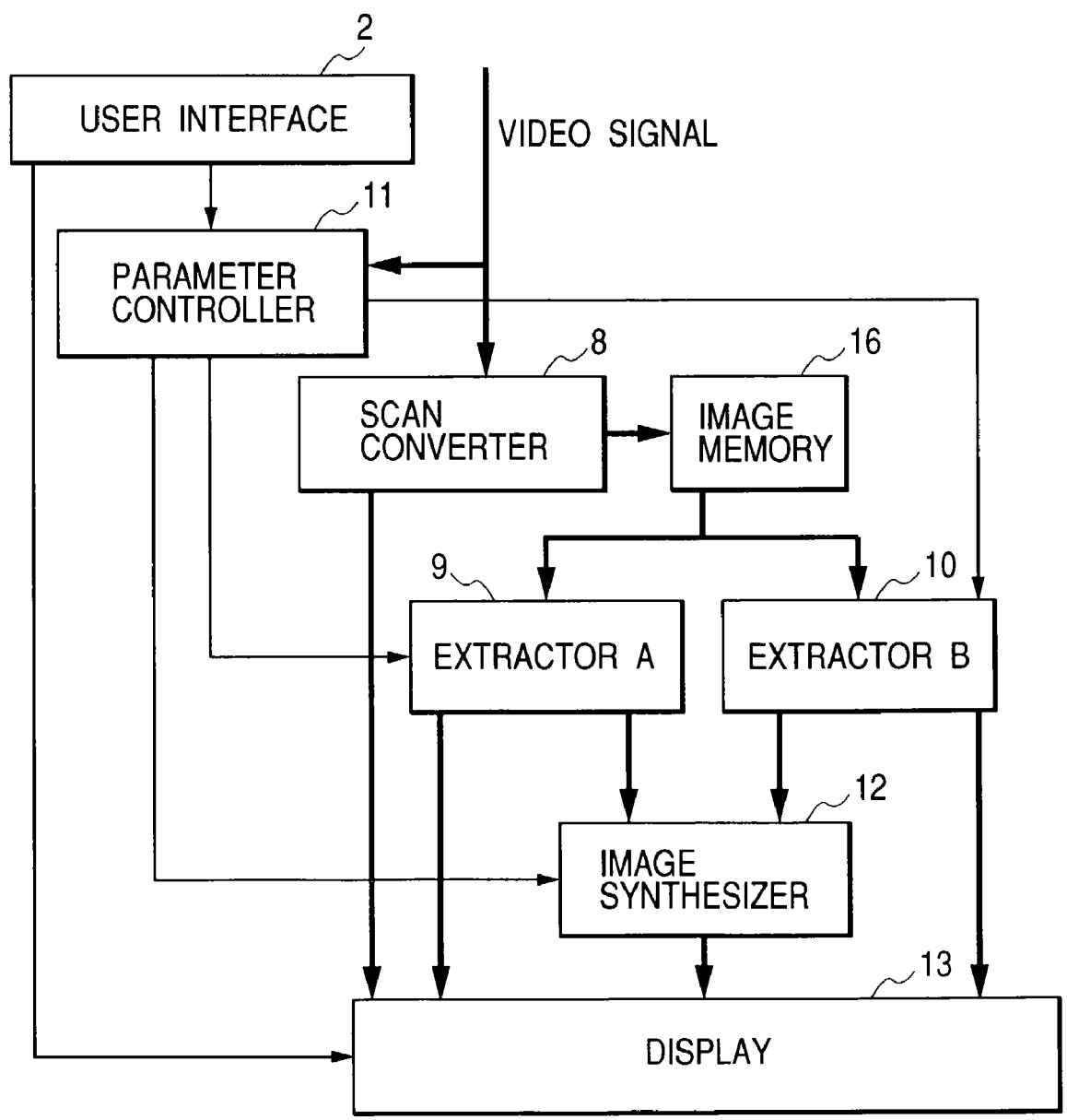
FIG. 13 is a diagram showing-an example of the configuration of an ultrasonic imaging system of the first embodiment of the invention.

Specifically, as shown in FIG. 13, an output of the scan converter 8 is stored into an image memory 16 and structure and texture emphasis is performed on the stored image and the structure-emphasized image and the texture-emphasized image are combined by the above-described method. Since the ultrasonic imaging system is characterized by its real-time operation, the image memory 16 is a moving image memory. Obviously, it is also effective to adjust the parameters so as to be optimum to a series of motions of the subject such as movement of the heart and movement by breathing.

With respect to the image display method, other than the method of displaying an output of the image synthesizer 12, an output of the scan converter 8 can be directly displayed or a result of emphasis before image synthesis can be also displayed as it is. Particularly, since a change in the picture quality exerts an influence on diagnosis, there is always a user's need for comparison between a tomographic image before the emphasizing process and a tomographic image after the emphasizing process.

Figure 14:
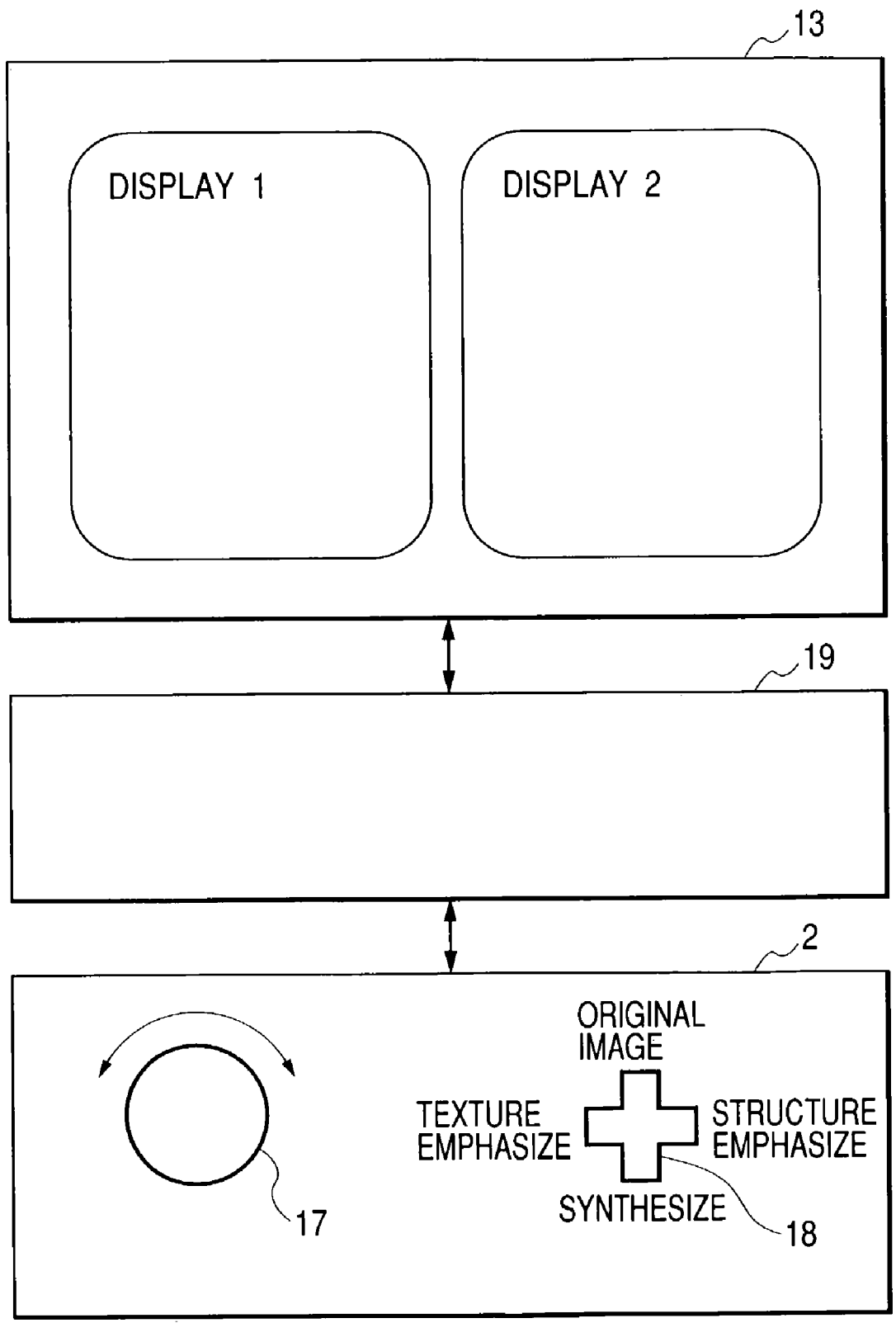
FIG. 14 is an external view of the ultrasonic imaging system of the first embodiment of the invention.

Therefore, in addition to the configuration that one of four kinds of image data pieces which can be input in FIG. 13 is selected and displayed in a whole screen, an effective configuration of the display, which is advantageous for the user, is that a plurality of images are displayed simultaneously. The image display and the user interface will be more concretely described with reference to FIG. 14 as follows.

First, the user selects an ultrasonic probe and sets an image target region. In response to the operation, default parameters are set on the system side, and an output of the scan converter is displayed as it is on the display screen 1 of the display unit. After that, the user selects the structure-emphasis mode by a mode selector 18 to display a structure-emphasized image in a display screen 2 next to the output of the scan converter of the display screen 1, and adjusts the structure-emphasis parameters by a setting knob 17. Since the parameter setting operation is performed easier when the target image does not change, it is important that the picture quality can be adjusted by using data stored in the image memory 16. According to the parameters, width of the weighting function is controlled and the weighting value is controlled by using similarity. At this time, the user can also use a known gain control knob (not shown).

After the structure emphasis parameter is determined, the texture emphasis mode is selected by the mode selector 18 to display a texture-emphasized image in the display screen 2 next to the output of the scan converter in the display screen 1, and a texture emphasis parameter is adjusted by the setting knob 17. In the case of a differential filter of a form such that the intensity of the differential filter is [1 −a] or [−1 a −1], the value "a" is controlled.

After the texture emphasis parameter is determined, the user selects an emphasis results combining mode by the mode selector 18. In this mode, the output of the scan converter and a synthesized image (which is an object image of the invention obtained by combining a structure-emphasized image and a texture-emphasized image) are displayed in the neighboring display screens 1 and 2, and the gain curve of each element is adjusted by the setting knob 17 so that a portion of weak signal intensity in an image can be also clearly seen, that is, an effective dynamic range of each image is widened.

In the case where the user is unsatisfied with the adjustment, the user can always return to the previous mode by the mode selector 18 and re-adjusts the structure emphasis parameter and/or the texture emphasis parameter.

In the first embodiment of the invention, the degree of emphasis of structure and texture can be independently and arbitrarily adjusted. Consequently, as if the system has two control means such as accelerator and a brake, the operator can easily adjust an image to meet his/her preferences.

Second Embodiment

Figure 9:
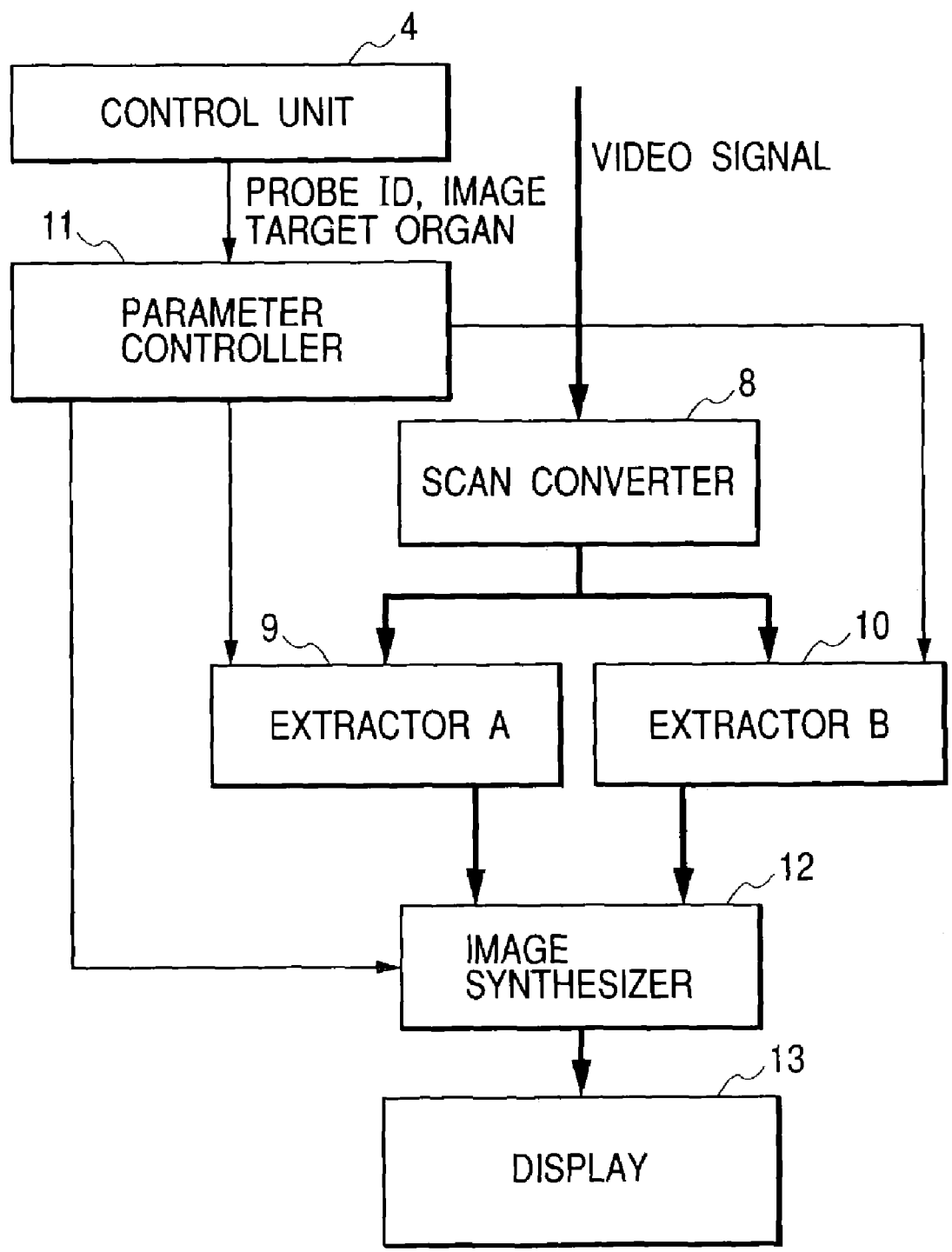
FIG. 9 is a diagram showing an example of the configuration of an ultrasonic imaging system of a second embodiment of the invention.

FIG. 9 is a diagram showing an example of the configuration of an ultrasonic imaging system of a second embodiment of the invention. In the system of the second embodiment, the control unit 4 sets parameters such as probe parameters, image target region, and imaging parameters in the parameter controller 11. By using not image statistical information but parameter values preliminarily set according to cases such as the probe parameters, image target region, and imaging parameters as parameters input to the parameter controller 11, the speed of the imaging process can be increased.

The probe parameters include, concretely, probe ID, center frequency used and, in the case of using a convex probe or sector probe, deflection angle. The imaging parameters are, concretely, factors exerting an influence on statistical information of an intensity difference between pixels of an original image depending on whether tissue harmonic imaging (second harmonic imaging) or compound imaging.

Since the probe parameters are important factors to determine the shape of a point response function, it also exerts a large influence on generation of an interference pattern described above.

The tissue harmonic imaging is imaging for extracting a frequency component which is twice as high as a transmit frequency positively using nonlinear propagation in a living body from a reception signal. The bandwidth of the received frequency is different from that of the transmit frequency and the shape of the point response function changes. Particularly, generation of the nonlinear component is proportional to the square of sound pressure. Consequently, an unnecessary signal of which sound pressure is not high enough to generate a nonlinear component such as multiple reflection in a living body decreases in the bandwidth of the double frequency of the reception signal and is characterized in that the component of the structure of a tissue in a living body is seen more easily. Therefore, at the time of performing extraction (structure emphasis) of a component emphasizing the structure of a tissue in a living body and extraction (texture emphasis) of extracting a texture component, a large influence is exerted on the degree of emphasis of the two components.

Similarly, the compound imaging is an imaging method of combining a plurality of tomographic images of smaller variations in the structure components as compared with variations in an interference pattern such as frequency, deflection angle, and slice direction. As a result of the compound imaging, the structure component is enhanced and the texture component decreases. Depending on whether the system enters the compound imaging mode or not, the necessary degree of structure emphasis and that of texture emphasis change.

Third Embodiment

Figure 10:
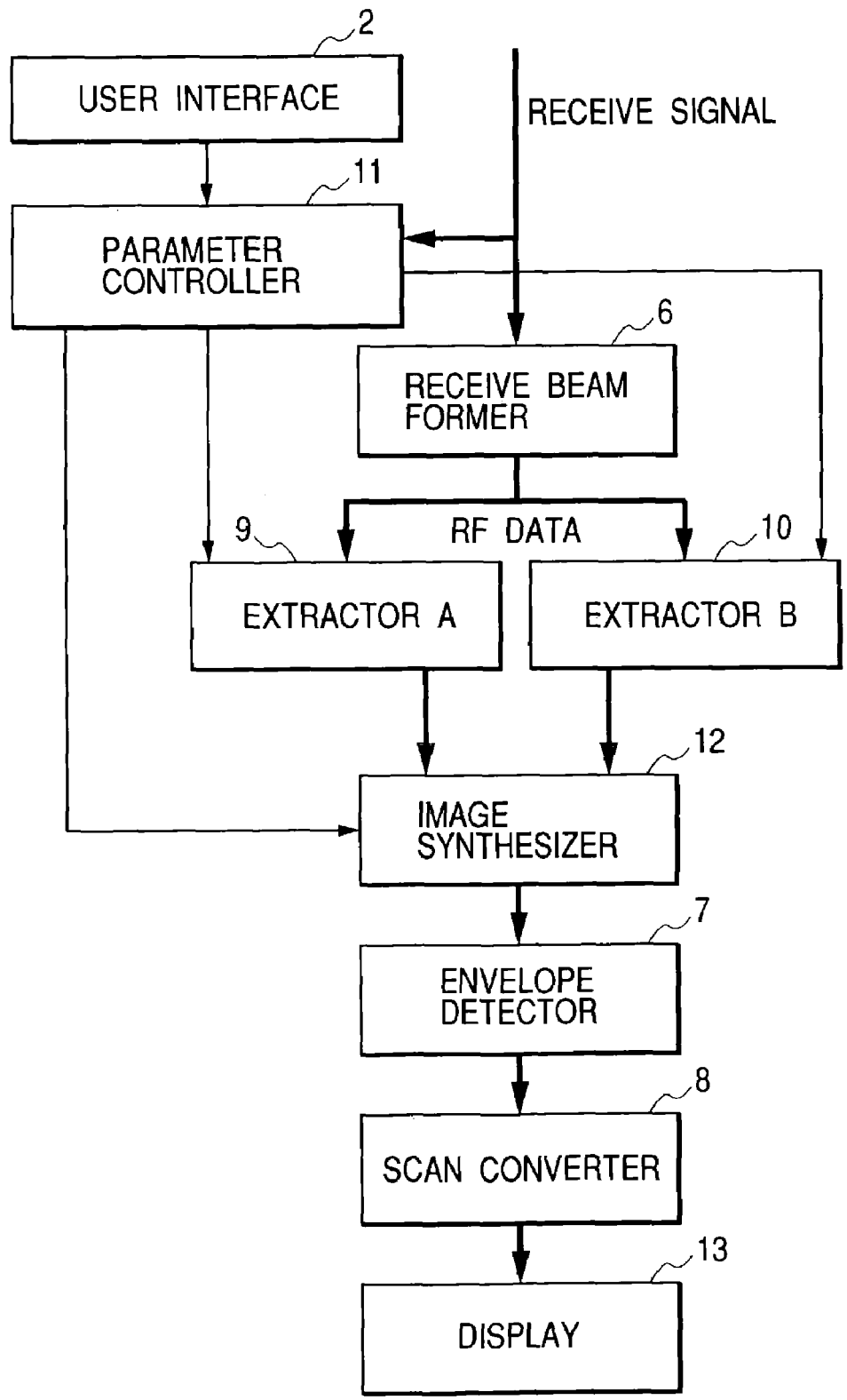
FIG. 10 is a diagram showing an example of the configuration of an ultrasonic imaging system of a third embodiment of the invention.

FIG. 10 is a diagram showing an example of the configuration of an ultrasonic imaging system of a third embodiment of the invention. In the configuration shown in FIG. 10, in place of outputting a video signal output from the envelope detector 7 shown in FIG. 3 to the memory of the parameter controller 11 in the modification of the first embodiment shown in FIG. 4, a reception signal supplied to the receive beam former 6 via the transmit/receive switch 5 shown in FIG. 3 is output to the memory of the parameter controller 11. RF data output from the receive beam former 6 is sent to the structure extractor (extractor A) 9 and stored in the memory and is also sent to the texture extractor (extractor B) 10 and stored in the memory. The parameter controller 11 calculates the above-described statistical information of the RF signal, that is, the width of the histogram of the intensity difference.

By using the statistical information, the RF data, and the parameters set in the parameter controller 11, the structure extractor (extractor A) 9 extracts structure-emphasized image data in which the structure of a tissue in a living body is emphasized. The texture extractor (extractor B) 10 extracts texture-emphasized image data in which a texture pattern coming from the properties of the tissue in a living body is emphasized in a manner similar to the first embodiment. The image synthesizer 12 combines the structure-emphasized image data and the texture-emphasized image data, thereby obtaining synthesized image data. An output of the image synthesizer 12 is detected by the envelope detector 7 and is converted into a video signal. The video signal is supplied to the scan converter 8 and converted into image data (B-mode image data) The image data of the synthesized image is sent to the display 13 and displayed.

Forth Embodiment

Figure 11:
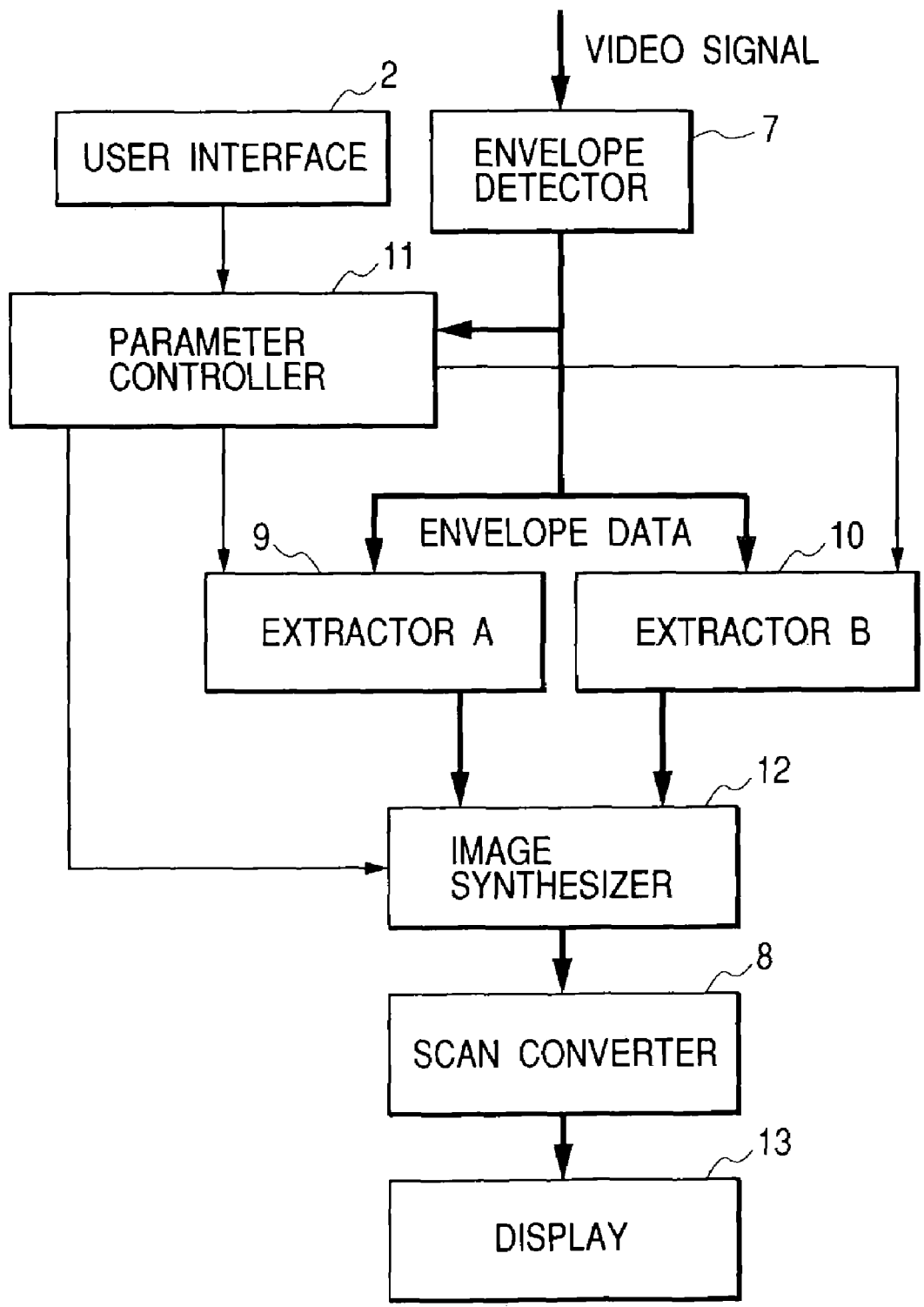
FIG. 11 is a diagram showing an example of the configuration of an ultrasonic imaging system of a fourth embodiment of the invention.

FIG. 11 is a diagram showing an example of the configuration of an ultrasonic imaging system of a fourth embodiment of the invention.

In the configuration shown in FIG. 11, in place of outputting the video signal output from the envelope detector 7 shown in FIG. 3 to the memory of the parameter controller 11 in the modification of the first embodiment shown in FIG. 4, the video signal input to the envelope detector 7 shown in FIG. 3 is output to the memory of the parameter controller 11. Envelope data output from the envelope detector 7 is sent to the structure extractor (extractor A) 9 and stored in the memory, and is also sent to the texture extractor (extractor B) 10 and stored in the memory. The parameter controller 11 calculates the above-described statistical information of envelope data, that is, the width of the histogram of the intensity difference. By using the statistical information and the parameters set in the parameter controller 11, the structure extractor (extractor A) 9 extracts structure-emphasized image data in which the structure of a tissue in a living body is emphasized. The texture extractor (extractor B) 10 extracts texture-emphasized image data in which a texture pattern coming from the properties of the tissue in a living body is emphasized in a manner similar to the first embodiment. The image synthesizer 12 combines the structure-emphasized image data and the texture-emphasized image data, thereby obtaining synthesized image data. An output of the image synthesizer 12 is detected by the envelope detector 7 and is converted into a video signal. The video signal is supplied to the scan converter 8 and converted into image data (B-mode image data). The image data of the synthesized image is sent to the display 13 and displayed.

In the third and fourth embodiments, as shown in FIGS. 10 and 11, respectively, the extracting process is performed before execution of the process by the scan converter 8. From the viewpoint of computation speed, it is desirable to extract the structure-emphasized image data and the texture-emphasized image data by using an output of the scan converter 8 of which information amount is reduced as much as possible. However, when considering optimization of the filter process in accordance with the shape of the point response function, it is more desirable to execute the process of extracting the structure-emphasized image data and the texture-emphasized image data before execution of the scan by the scan converter 8.

The structure-emphasized image data and the texture-emphasized image data is extracted by using a receive signal in the third embodiment and by using an envelope signal in the fourth embodiment. It is sufficient to sequentially store two-dimensional data obtained by sampling the receive signal/envelope signal corresponding to each scanning line on the time base as target data from which the structure-emphasized image data/texture-emphasized image data is extracted as described in the first embodiment into the memories of the structure extractor (extractor A) 9 and the texture extractor (extractor B) 10 concurrently with execution of reception and transmission of the ultrasonic pulse. The decimation process can be also performed in a manner similar to the first embodiment. The further description will not be repeated.

The point response function is considered here for the following reason. Generation of an interference pattern and the shape of point response function are deeply related to each other. In the case of using a convex probe or sector probe, after converting the two-dimensional image data obtained by ultrasonic scanning of a radiation shape or fan shape into two-dimensional image data in a square lattice shape, the size and shape of the point response function changes according to the distance from the probe to the focal position. Since the shape of the point response function obtained from envelope data and that of the point response function obtained from RF data are largely different from each other, the structure of a tissue in a living body obtained from the RF data having a sharp point response function shape becomes shape. However, an influence of the interference pattern is also large, so that the role of the above-described structure extracting filter is large.

As described in the first embodiment, also in the third and fourth embodiments, it is also effective method of providing the RF data storing memory and the envelope data storing memory and, after reception of ultrasonic waves for obtaining data for a tomographic image, capable of adjusting an image so as to be optimum to the operator.

Fifth Embodiment

Figure 12:
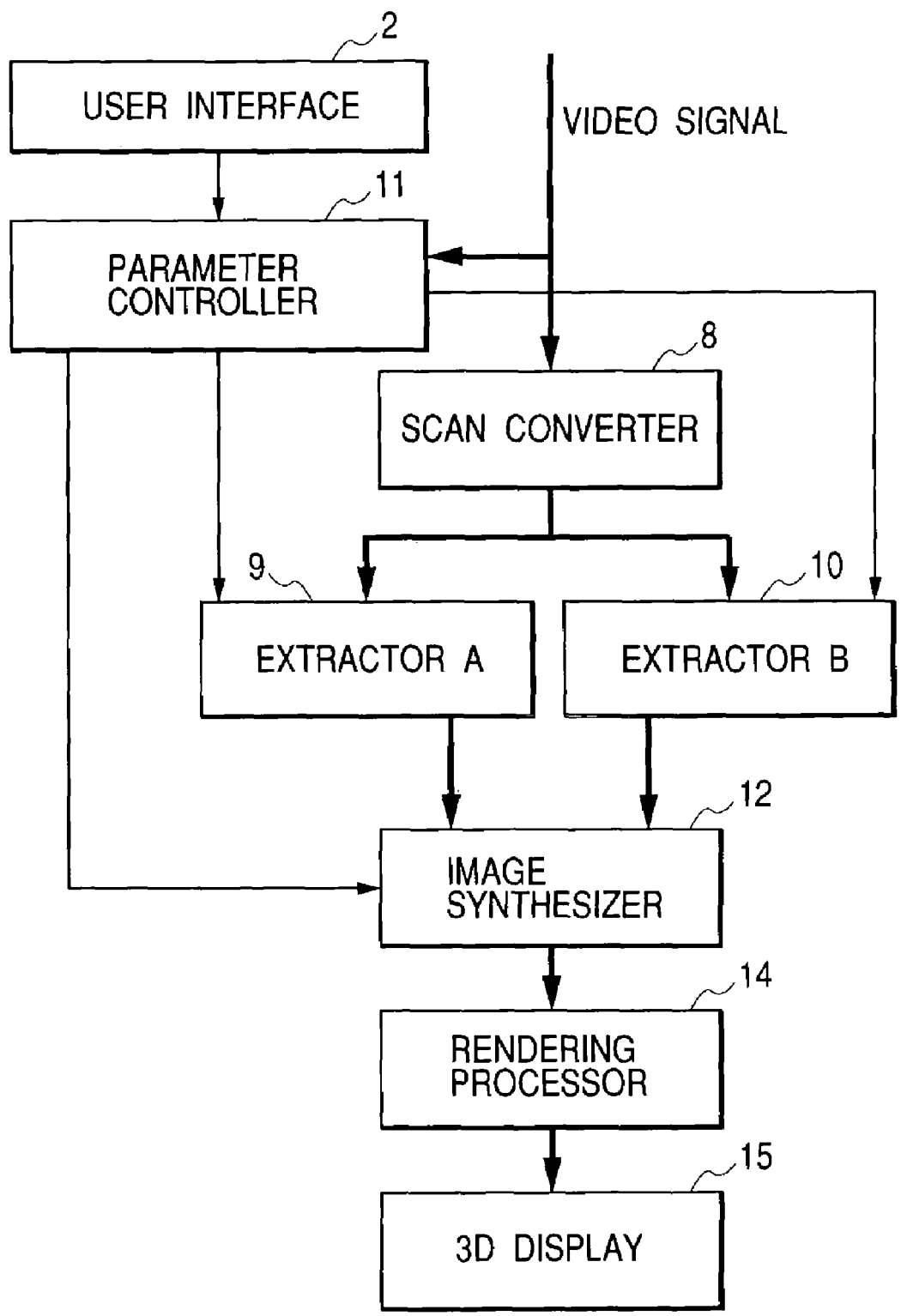
FIG. 12 is a diagram showing an example of the configuration of an ultrasonic imaging system of a fifth embodiment of the invention.

FIG. 12 is a diagram showing an example of the configuration of an ultrasonic imaging system of a fifth embodiment of the invention. The fourth embodiment relates to the ultrasonic imaging system for obtaining a three-dimensional ultrasonic image of a living body. The system of the fifth embodiment has a configuration obtained by modifying the configuration shown in FIG. 4 and has a rendering processor 14 for performing various known rendering processes for generating data for three-dimensionally displaying an image target region of a living body by using an output of the image synthesizer 12. A three-dimensional ultrasonic image of the image target region obtained by the rendering processor 14 is displayed on a three-dimensional (3D) display 15.

By using an ultrasonic probe in which ultrasonic elements are arranged two-dimensionally or by mechanically moving an ultrasonic probe-in which ultrasonic elements are arranged one-dimensionally in the direction perpendicularly crossing the beam scanning direction, an echo signal from a living body can be collected as three-dimensional data. When a signal process is performed by using an echo signal on which the above-described interference pattern is multiplexed and the rendering process is performed, at the time of addition (integration) in the projection direction of the three-dimensional image data, the difference between addition (integration) in a path of a region of a large influence of the interference pattern and addition (integration) in a path of a region of a small influence of the interference pattern exerts an influence on the region in which the interference pattern exists and the other region, so that artifact occurs. Particularly, in the case of executing surface rendering, a surface shape of a living body is influenced by the interference pattern. In the invention, however, as described in the first embodiment, the operator can arbitrarily and independently adjust the degree of emphasis with respect to extraction of structure-emphasized image data (structure-emphasized image) and extraction of texture-emphasized image data (texture-emphasized image) As if the system has two control means like an accelerator and a brake, the operator can easily adjust the emphasis of a three-dimensional ultrasonic image in accordance with his/her preferences. According to the fifth embodiment, the three-dimensional ultrasonic image can be substantially changed.

FIGS. 15(A) to 15(D) show an example of an image actually processed by the method of the invention.

FIG. 15(A) shows an original image-which is not yet subjected to the process of the invention. FIG. 15(B) shows an image subjected to the structure emphasis, in which an interference pattern is generally suppressed and the contours of a linear structure of high intensity extending laterally in the upper part of the image and a circular structure in the upper right part are emphasized without being blurred. FIG. 15(C) shows a texture-emphasized image which plays a role of interpolating the image of FIG. 15(B). FIG. 15(D) is a synthesized image obtained by combining the structure-emphasized image of FIG. 15(B) and the texture-emphasized image of FIG. 15(C), in which the structures are emphasized and texture information properly remains.

According to the invention, the balance between extraction of a structure and extraction of a texture in a living body can be easily adjusted. The invention can provide the ultrasonic imaging system and method in which the balance can be adjusted by the operator. The operator can effectively extract information in which a structure of a tissue of a living body of an ultrasonic image on which an interference pattern of ultrasonic waves is multiplexed is reflected, easily properly extract texture information, and obtain a single ultrasonic image including information necessary for diagnosis.

The foregoing embodiments can be applied to tissue harmonic imaging and compound imaging. The invention is not limited to the foregoing embodiments but can be variously modified without departing from the scope of the technical ideas.

In each of the foregoing embodiments, by a configuration of storing a plurality of frames (images) of RF signals or video signals, two synthesized images obtained with different weighting values may be obtained and displayed. Thus, the user can grasp information useful for diagnosis.

The invention also includes the following configurations.
1. An ultrasonic imaging method for transmitting an ultrasonic pulse to a living body, receiving the ultrasonic pulse reflected by the living body, and obtaining B mode image data of the living body, including: a structure extracting step of extracting structure-emphasized image data in which a structure of a tissue in the living body is emphasized from the B-mode image data; a texture pattern extracting step of extracting texture-emphasized image data in which a texture pattern coming from properties of a tissue in the living body is emphasized from the B-mode image data; an image synthesizing step of obtaining a synthesized image by weighting and combining the structure-emphasized image data and the texture-emphasized image data; and a display for displaying at least one of the structure-emphasized image data, the texture-emphasized image data, and the synthesized image.
2. The ultrasonic imaging method according to the item 1, wherein in the structure extracting step, a structure of a living body tissue constructed by a set of point reflectors which are continuously distributed in at least one direction in the living body is extracted.
3. The ultrasonic imaging method according to the item 1, wherein in the texture pattern extracting step, a component coming from a reflector constructed by a set of point reflectors which are not continuously distributed in the living body but are spread is extracted.
4. The ultrasonic imaging method according to the item 1, wherein the structure extracting step includes: a step of determining a region of peripheral pixels of each pixel in the B-mode image data; a step of obtaining a function for determining a weighting function on the basis of the difference between intensity of the each pixel and intensity of each of the peripheral pixels; a step of determining the weighting function for each of the peripheral pixels from differentiation of the function; and a step of using a value obtained by adding a sum of products of the weighting function and intensity of each of the peripheral pixels to intensity of each of pixels of the B-mode image data as signal intensity of each of pixels of the structure-emphasized image data, the function has a maximum point when it is 0, and an integral value of an absolute value of the function in a region from negative infinity to positive infinity is finite.
5. The ultrasonic imaging method according to the item 1, further including a parameter controlling step of setting parameters for signal processing in the structure extracting step, the texture pattern extracting step, and the image synthesizing step on the basis of a distribution of signal intensities of pixels in the same frame of the B-mode image data.
6. The ultrasonic imaging method according to the item 1, wherein the texture pattern extracting step emphasizes the texture pattern by using a differential filter in two directions of signal intensities of pixels in the same frame of the B-mode image data.
7. An ultrasonic imaging method including: a transmitting step of transmitting an ultrasonic pulse from an ultrasonic probe having a plurality of ultrasonic elements to a living body on the basis of a transmit signal of an ultrasonic wave output from a transmit beam former; a transmit/receive switching step of switching transmission and reception of the ultrasonic wave from the ultrasonic probe; a receive step of receiving an ultrasonic pulse reflected from the living body by the ultrasonic probe; a step of generating an RF signal as a receive beam signal from a signal received by the ultrasonic probe by a receive beam former and outputting the RF signal; a step of detecting an envelope of the RF signal and outputting the envelope as a video signal; a step of inputting the video signal to a scan converter; a step of extracting structure-emphasized image data in which a structure of a tissue in the living body is emphasized from an output of the scan converter; a texture pattern extracting step of extracting texture-emphasized image data in which a texture pattern coming from properties of a tissue in the living body is emphasized from an output of the scan converter; an image synthesizing step of obtaining a synthesized image by weighting and combining the structure-emphasized image data and the texture-emphasized image data; a parameter controlling step of setting parameters for signal processing into the structure extracting step, the texture pattern extracting step, and the image synthesizing step; an input step of receiving the parameters for signal processing and setting the parameters for signal processing into the parameter controlling step; a control step of controlling the transmitting step, the transmit/receive switching step, and the receiving step on the basis of the control parameters supplied in the input step; and a display step of displaying at least one of the structure-emphasized image data, the texture-emphasized image data, and the synthesized image.
8. The ultrasonic imaging method according to the item 7, wherein the parameter controlling step sets the parameters for signal processing on the basis of the video signal.
9. The ultrasonic imaging method according to the item 7, wherein in the control step, information regarding the ultrasonic probe and information regarding an image target region in the living body is set in the parameter controlling step.
10. The ultrasonic imaging method according to the item 7, further comprising a rendering step of generating data for three-dimensionally displaying an image target region in the living body from an output of the image synthesizing step, wherein the image target region in the living body is three-dimensionally displayed in the display step.

11. An ultrasonic imaging step including: a transmitting step of transmitting an ultrasonic pulse from an ultrasonic probe having a plurality of ultrasonic elements to a living body on the basis of a transmit signal of ultrasonic wave output from a transmit beam former; a transmit/receive switching step of switching transmission and reception of the ultrasonic wave to/from the ultrasonic probe; a receiving step of receiving the ultrasonic pulse reflected from the living body by the ultrasonic probe; a step of generating an RF signal as a receive beam signal from a signal received by the ultrasonic probe and outputting the RF signal by a receive beam former; a structure extracting step of extracting structure-emphasized image data in which a structure of a tissue in the living body is emphasized from the RF signal; a texture pattern extracting step of extracting texture-emphasized image data in which a texture pattern coming from properties of a tissue in the living body is emphasized from the RF signal; an image synthesizing step of obtaining a synthesized image by weighting and combining the structure-emphasized image data and the texture-emphasized image data; an envelope detecting step of detecting an envelope of an output signal in the image synthesizing step and outputting the envelope as a video signal; a step of inputting the video signal to a scan converter; a parameter controlling step of setting parameters for signal processing in the structure extracting step, the texture pattern extracting step, and the image synthesizing step; an input step of receiving the parameters for signal processing and setting the parameters for signal processing in the parameter controlling step; a control step of controlling the transmitting step, the transmit/receive switching step, and the receiving step on the basis of the control parameters supplied from the input unit; and a display step of displaying at least one of the structure-emphasized image data, the texture-emphasized image data, and the synthesized image.

12. The ultrasonic imaging method according to the item 11, wherein in the parameter controlling step, the parameters for signal processing are set on the basis of the receive signal.

13 An ultrasonic imaging method including: a transmitting step of transmitting an ultrasonic pulse from an ultrasonic probe having a plurality of ultrasonic elements on the basis of a transmit signal of an ultrasonic wave output from a transmit beam former; a transmit/receive switching step of switching transmission and reception of the ultrasonic wave to/from the ultrasonic probe; a receiving step of receiving the ultrasonic pulse reflected by the living body from the ultrasonic probe; a step of generating an RF signal as a receive beam signal from a signal received from the ultrasonic probe and outputting the RF signal by a receive beam former; an envelope detecting step of detecting an envelope of the RF signal and outputting the envelope as a video signal; a structure extracting step of extracting structure-emphasized image data in which a structure of a tissue in the living body is emphasized from the video signal; a texture pattern extracting step of extracting texture-emphasized image data in which a texture pattern coming from properties of a tissue in the living body is emphasized from the video signal; an image synthesizing step of obtaining a synthesized image by weighting and combining the structure-emphasized image data and the texture-emphasized image data; a step of inputting an output signal of the image synthesizing step as a video signal to a scan converter; a parameter controlling step of setting parameters for signal processing in the structure extracting step, the texture pattern extracting step, and the image synthesizing step; an input step of receiving the parameters for signal processing and setting the parameters for signal processing in the parameter controlling step; a control step of controlling the transmitting step, the transmit/receive switching step, and the receiving step on the basis of the control parameters supplied from the input step; and a display step of displaying at least one of the structure-emphasized image data, the texture-emphasized image data, and the synthesized image.

14. The ultrasonic imaging method according to the item 13, wherein in the parameter controlling step, the parameters for signal processing are set on the basis of the video signal.

15. An ultrasonic imaging method of transmitting an ultrasonic pulse to a living body, receiving the ultrasonic pulse reflected by the living body, and obtaining B-mode image data of the living body, including: a structure extracting step of extracting structure-emphasized image data in which a structure of a tissue of the living body is emphasized by using data of the B-mode image; a texture pattern extracting step of extracting texture-emphasized image data in which a texture pattern coming from properties of a tissue in the living-body is emphasized by using the B-mode image data in parallel with the structure extracting step; an image synthesizing step of obtaining a synthesized image by weighting and combining the structure-emphasized image data and the texture-emphasized image data; and a display step of displaying at least one of the structure-emphasized image data, the texture-emphasized image data, and the synthesized image.

The present invention can provide an ultrasonic imaging system and method capable of extracting structure-emphasized image data in which the structure of a tissue in a living body is emphasized and texture-emphasized image data in which a texture pattern coming from properties of the tissue in the living body is emphasized from B-mode image data and obtaining a synthesized image obtained by weighting and combining the extracted two image data pieces.

What is claimed is:

1. An ultrasonic imaging system for transmitting an ultrasonic pulse to a living body, receiving the ultrasonic pulse reflected by said living body, and obtaining B-mode image data of said living body, comprising:

a structure extractor for extracting structure-emphasized image data in which a structure of a tissue in said living body is emphasized from said B-mode image data;

a texture pattern extractor for extracting texture-emphasized image data in which a texture pattern coming from properties of a tissue in said living body is emphasized from said B-mode image data;

an image synthesizer for obtaining a synthesized image by weighting and combining said structure-emphasized image data and said texture-emphasized image data; and a display for displaying at least one of said structure-emphasized image data, said texture-emphasized image data, and said synthesized image;

wherein said structure extractor and said texture pattern extractor extract said structure-emphasized image data and said texture-emphasized image data, respectively, from the same B-mode image data.

2. The ultrasonic imaging system according to claim 1, wherein two synthesized images to which different weights are assigned are displayed side by side.

3. The ultrasonic imaging system according to claim 1, wherein said structure extractor extracts a structure of a living body tissue constructed by a set of point reflectors which are continuously distributed in at least one direction in said living body.

4. The ultrasonic imaging system according to claim 1, wherein said texture pattern extractor extracts a component coming from a reflector constructed by a set of point reflectors which are not continuously distributed in said living body but are spread.

5. The ultrasonic imaging system according to claim 1, wherein said structure extractor comprises:
   means for determining a region of peripheral pixels of each pixel in said B-mode image data; and
   means for obtaining a function for determining a weighting function on the basis of the difference between intensity of said each pixel and intensity of each of said peripheral pixels,
   said function has a maximum point when it is 0,
   an integral value of an absolute value of said function in a region from negative infinity to positive infinity is finite,
   said weighting function on each of said peripheral pixels is determined from differentiation of said function, and
   a value obtained by adding a sum of products of said weighting function and intensity of each of said peripheral pixels to intensity of each of pixels of said B-mode image data is used as signal intensity of each of pixels of said structure-emphasized image data.

6. The ultrasonic imaging system according to claim 1, further comprising a parameter controller for setting parameters for signal processing into said structure extractor, said texture pattern extractor, and said image synthesizer on the basis of a distribution of signal intensities of pixels in the same frame of said B-mode image data.

7. The ultrasonic imaging system according to claim 1, wherein said texture pattern extractor emphasizes said texture pattern by using a differential filter in two directions of signal intensities of pixels in the same frame of said B-mode image data.

8. An ultrasonic imaging system comprising:
   an ultrasonic probe having a plurality of ultrasonic elements, for transmitting an ultrasonic pulse to a living body, and receiving the ultrasonic pulse reflected by said living body;
   a transmit beam former for outputting a transmit signal of an ultrasonic wave transmitted from said ultrasonic probe;
   a receive beam former for generating an RF signal as a receive beam signal from a signal received from said ultrasonic probe and outputting the RF signal;
   a transmit/receive switch for switching transmission and reception of the ultrasonic wave to/from said ultrasonic probe;
   an envelope detector for detecting an envelope of said RF signal and outputting the envelope as a video signal;
   a scan converter to which said video signal is input;
   a structure extractor for extracting structure-emphasized image data in which a structure of a tissue in said living body is emphasized from an output of said scan converter;
   a texture pattern extractor for extracting texture-emphasized image data in which a texture pattern coming from properties of a tissue in said living body is emphasized from an output of said scan converter;
   an image synthesizer for obtaining a synthesized image by weighting and combining said structure-emphasized image data and said texture-emphasized image data;
   a parameter controller for setting parameters for signal processing into said structure extractor, said texture pattern extractor, and said image synthesizer;
   an input unit for receiving said parameters for signal processing and setting said parameters for signal processing into said parameter controller;
   a control unit for controlling said transmit beam former, said transmit/receive switch, and said receive beam former on the basis of the control parameters supplied from said input unit; and
   a display for displaying at least one of said structure-emphasized image data, said texture-emphasized image data, and said synthesized image;
   wherein said structure extractor and said texture pattern extractor extract said structure-emphasized image data and said texture-emphasized image data, respectively, from the same B-mode image data.

9. The ultrasonic imaging system according to claim 8, wherein said parameter controller sets said parameters for signal processing on the basis of said video signal.

10. The ultrasonic imaging system according to claim 8, wherein said control unit sets information regarding said ultrasonic probe and information regarding an image target region in said living body into said parameter controller.

11. The ultrasonic imaging system according to claim 8, further comprising a rendering processor for generating data for three-dimensionally displaying an image target region in said living body from an output of said image synthesizer,
   wherein said image target region in said living body is three-dimensionally displayed on said display.

12. An ultrasonic imaging system comprising,
   an ultrasonic probe having a plurality of ultrasonic elements, for transmitting an ultrasonic pulse to a living body, and receiving the ultrasonic pulse reflected by said living body;
   a transmit beam former for outputting a-transmit signal of an ultrasonic wave transmitted from said ultrasonic probe;
   a receive beam former for generating an RF signal as a receive beam signal from a signal received by said ultrasonic probe and outputting the RF signal;
   a transmit/receive switch for switching transmission and reception of the ultrasonic wave to/from said ultrasonic probe;
   a structure extractor for extracting structure-emphasized image data in which a structure of a tissue in said living body is emphasized from said RF signal;
   a texture pattern extractor for extracting texture-emphasized image data in which a texture pattern coming from properties of a tissue in said living body is emphasized from said RF signal;
   an image synthesizer for obtaining a synthesized image by weighting and combining said structure-emphasized image data and said texture-emphasized image data;
   an envelope detector for detecting an envelope of an output signal of said image synthesizer and outputting the envelope as a video signal;
   a scan converter to which said video signal is input;
   a parameter controller for setting parameters for signal processing into said structure extractor, said texture pattern extractor, and said image synthesizer;
   an input unit for receiving said parameters for signal processing and setting said parameters for signal processing into said parameter controller;
   a control unit for controlling said transmit beam former, said transmit/receive switch, and said receive beam former on the basis of the control parameters supplied from said input unit; and a display for displaying at least one of said structure-emphasized image data, said texture-emphasized image data, and said synthesized image;

wherein said structure extractor and said texture pattern extractor extract said structure-emphasized image data and said texture-emphasized image data, respectively, from the same B-mode image data.

13. The ultrasonic imaging system according to claim 12, wherein said parameter controller sets said parameters for signal processing on the basis of said receive signal.

14. An ultrasonic imaging system comprising:
an ultrasonic probe having a plurality of ultrasonic elements, for transmitting an ultrasonic pulse to a living body, and receiving the ultrasonic pulse reflected by said living body;
a transmit beam former for outputting a transmit signal of an ultrasonic wave transmitted from said ultrasonic probe;
a receive beam former for generating an RF signal as a receive beam signal from a signal received from said ultrasonic probe and outputting the RF signal;
a transmit/receive switch for switching transmission and reception of the ultrasonic wave to/from said ultrasonic probe;
an envelope detector for detecting an envelope of said RF signal and outputting the envelope as a video signal;
a structure extractor for extracting structure-emphasized image data in which a structure of a tissue in said living body is emphasized from said video signal;
a texture pattern extractor for extracting texture-emphasized image data in which a texture pattern coming from properties of a tissue in said living body is emphasized from said video signal;
an image synthesizer for obtaining a synthesized image by weighting and combining said structure-emphasized image data and said texture-emphasized image data;
a scan converter to which an output signal of said image synthesizer is input as a video signal;
a parameter controller for setting parameters for signal processing into said structure extractor, said texture pattern extractor, and said image synthesizer;
an input unit for receiving said parameters for signal processing and setting said parameters for signal processing into said parameter controller;
a control unit for controlling said transmit beam former, said transmit/receive switch, and said receive beam former on the basis of the control parameters supplied from said input unit; and
a display for displaying at least one of said structure-emphasized image data, said texture-emphasized image data, and said synthesized image;
wherein said structure extractor and said texture pattern extractor extract said structure-emphasized image data and said texture-emphasized image data, respectively, from the same B-mode image data.

15. The ultrasonic imaging system according to claim 14, wherein said parameter controller sets said parameters for signal processing on the basis of said video signal.

16. An ultrasonic imaging system for transmitting an ultrasonic pulse to a living body, receiving the ultrasonic pulse reflected by said living body, and obtaining B-mode image data of said living body, comprising:
a structure extractor for extracting structure-emphasized image data in which a structure of a tissue of said living body is emphasized by using data of said B-mode image;
a texture pattern extractor for extracting texture-emphasized image data in which a texture pattern coming from properties of a tissue in said living body is emphasized by using said B-mode image data in parallel with said structure extractor;
an image synthesizer for obtaining a synthesized image by weighting and combining said structure-emphasized image data and said texture-emphasized image data; and
a display for displaying at least one of said structure-emphasized image data, said texture-emphasized image data, and said synthesized image;
wherein said structure extractor and said texture pattern extractor extract said structure-emphasized image data and said texture-emphasized image data, respectively, from the same B-mode image data.

17. An ultrasonic imaging system having means of transmitting an ultrasonic pulse to a living body, receiving the ultrasonic pulse reflected by said living body, and obtaining B-mode image data of said living body, a structure extractor for extracting structure-emphasized image data in which a structure of a tissue in said living body is emphasized from said B-mode image data, and a display for displaying said structure-emphasized image data,
wherein said structure extractor comprises:
means for determining a region of peripheral pixels of each pixel of said B-mode image data; and
means for obtaining a function for determining a weighting function on the basis of the difference between intensity of said each pixel and intensity of each of said peripheral pixels,
said function has a maximum point when it is 0,
an integral value of an absolute value of said function in a region from negative infinity to positive infinity is finite,
said weighting function for each of said peripheral pixels is determined from differentiation of said function, and
a value obtained by adding a sum of products of said weighting function and intensity of each of said peripheral pixels to intensity of each of pixels of said B-mode image data is used as signal intensity of each of pixels of said structure-emphasized image data.

18. The ultrasonic signal processing method according to claim 17, wherein said structure extractor and said texture pattern extractor extract said structure-emphasized image data and said texture-emphasized image data, respectively, from the same B-mode image data.

19. An ultrasonic imaging system for transmitting an ultrasonic pulse to a living body, receiving the ultrasonic pulse reflected by said living body, and obtaining B-mode image data of said living body, comprising:
a structure extractor for extracting structure-emphasized image data in which a structure of a tissue in said living body is emphasized from said B-mode image data;
a texture pattern extractor for extracting texture-emphasized image data in which a texture pattern coming from properties of a tissue in said living body is emphasized from said B-mode image data;
an image synthesizer for obtaining a synthesized image by weighting and combining said structure-emphasized image data and said texture-emphasized image data; and
a display for displaying at least one of said structure-emphasized image data, said texture-emphasized image data, and said synthesized image;
wherein said structure extractor extracts a structure of a living body tissue constructed by a set of point reflectors which are continuously distributed in at least one direction in said living body.

20. An ultrasonic imaging system for transmitting an ultrasonic pulse to a living body, receiving the ultrasonic pulse reflected by said living body, and obtaining B-mode image data of said living body, comprising:
- a structure extractor for extracting structure-emphasized image data in which a structure of a tissue in said living body is emphasized from said B-mode image data;
- a texture pattern extractor for extracting texture-emphasized image data in which a texture pattern coming from properties of a tissue in said living body is emphasized from said B-mode image data;
- an image synthesizer for obtaining a synthesized image by weighting and combining said structure-emphasized image data and said texture-emphasized image data; and
- a display for displaying at least one of said structure-emphasized image data, said texture-emphasized image data, and said synthesized image;
- wherein said texture pattern extractor extracts a component coming from a reflector constructed by a set of point reflectors which are not continuously distributed in said living body but are spread.

21. An ultrasonic imaging system for transmitting an ultrasonic pulse to a living body, receiving the ultrasonic pulse reflected by said living body, and obtaining B-mode image data of said living body, comprising:
- a structure extractor for extracting structure-emphasized image data in which a structure of a tissue in said living body is emphasized from said B-mode image data;
- a texture pattern extractor for extracting texture-emphasized image data in which a texture pattern coming from properties of a tissue in said living body is emphasized from said B-mode image data;
- an image synthesizer for obtaining a synthesized image by weighting and combining said structure-emphasized image data and said texture-emphasized image data; and
- a display for displaying at least one of said structure-emphasized image data, said texture-emphasized image data, and said synthesized image;
- wherein said structure extractor comprises:
- means for determining a region of peripheral pixels of each pixel in said B-mode image data; and
- means for obtaining a function for determining a weighting function on the basis of the difference between intensity of said each pixel and intensity of each of said peripheral pixels,
- said function has a maximum point when it is 0,
- an integral value of an absolute value of said function in a region from negative infinity to positive infinity is finite,
- said weighting function on each of said peripheral pixels is determined from differentiation of said function, and
- a value obtained by adding a sum of products of said weighting function and intensity of each of said peripheral pixels to intensity of each of pixels of said B-mode image data is used as signal intensity of each of pixels of said structure-emphasized image data.

22. An ultrasonic imaging system for transmitting an ultrasonic pulse to a living body, receiving the ultrasonic pulse reflected by said living body, and obtaining B-mode image data of said living body, comprising:
- a structure extractor for extracting structure-emphasized image data in which a structure of a tissue in said living body is emphasized from said B-mode image data;
- a texture pattern extractor for extracting texture-emphasized image data in which a texture pattern coming from properties of a tissue in said living body is emphasized from said B-mode image data;
- an image synthesizer for obtaining a synthesized image by weighting and combining said structure-emphasized image data and said texture-emphasized image data; and
- a display for displaying at least one of said structure-emphasized image data, said texture-emphasized image data, and said synthesized image;
- wherein said texture pattern extractor emphasizes said texture pattern by using a differential filter in two directions of signal intensities of pixels in the same frame of said B-mode image data.

23. An ultrasonic imaging system for transmitting en ultrasonic pulse to a living body, receiving the ultrasonic pulse reflected by said living body, and obtaining B-mode image data of said living body, comprising:
- a structure extractor for extracting structure-emphasized image data in which a structure of a tissue in said living body is emphasized from said B-mode image data;
- a texture pattern extractor for extracting texture-emphasized image data in which a texture pattern coming from properties of a tissue in said living body is emphasized from said B-mode image data;
- an image synthesizer for obtaining a synthesized image by weighting and combining said structure-emphasized image data and said texture-emphasized image data; and
- a display for displaying at least one of said structure-emphasized image data, said texture-emphasized image data, and said synthesized image;
- wherein said structure extractor and said texture pattern extractor extract said structure-emphasized image data and said texture-emphasized image data, respectively, from the same B-mode image data, and
- wherein the B-mode image data is a single tomographic image.

* * * * *